US010259862B2

(12) United States Patent
Carter et al.

(10) Patent No.: US 10,259,862 B2
(45) Date of Patent: Apr. 16, 2019

(54) VEGF-BINDING PROTEIN FOR BLOCKADE OF ANGIOGENESIS

(71) Applicants: Children's Medical Center Corporation, Boston, MA (US); The General Hospital Corporation, Boston, MA (US); President and Fellows of Harvard College, Cambridge, MA (US)

(72) Inventors: Bob Carter, Belmont, MA (US); Jeng-Shin Lee, Lincoln, MA (US); Szofia S. Bullain, Tustin, CA (US); Richard C. Mulligan, Cambridge, MA (US)

(73) Assignees: Children's Medical Center Corporation, Boston, MA (US); The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/619,917

(22) Filed: Jun. 12, 2017

(65) Prior Publication Data
US 2018/0127483 A1    May 10, 2018

Related U.S. Application Data

(63) Continuation of application No. 14/239,687, filed as application No. PCT/US2012/051412 on Aug. 17, 2012, now Pat. No. 9,701,731.

(60) Provisional application No. 61/525,278, filed on Aug. 19, 2011.

(51) Int. Cl.
| | |
|---|---|
| *A61K 38/00* | (2006.01) |
| *A61K 38/16* | (2006.01) |
| *C07K 14/00* | (2006.01) |
| *C07K 14/71* | (2006.01) |
| *C07K 19/00* | (2006.01) |
| *C07K 14/475* | (2006.01) |

(52) U.S. Cl.
CPC .......... *C07K 14/71* (2013.01); *C07K 14/475* (2013.01); *A61K 38/00* (2013.01); *C07K 2319/30* (2013.01)

(58) Field of Classification Search
None
See application file for complete search history.

(56) References Cited

U.S. PATENT DOCUMENTS

| 6,100,071 A | 8/2000 | Davis-Smyth et al. |
| 7,087,411 B2 | 8/2006 | Daly et al. |
| 2004/0014667 A1 | 1/2004 | Daly et al. |
| 2006/0234347 A1 | 10/2006 | Harding et al. |
| 2009/0305971 A1 | 12/2009 | Sessa et al. |
| 2010/0331250 A1 | 12/2010 | Zhou et al. |

OTHER PUBLICATIONS

Benouchan et al. (2005). Anti-angiogenic strategies for cancer therapy (review). Intl. J. Oncology. 27:563-571.*
Shumizu et al. (2005). Antineovascular therapy, a novel antiangiogenic approach. Expert. Opin. Ther. Targets. 9(1):63-76.*
Auricchio et al., "Isolation of Highly Infectious and Pure Adeno-Associated Virus Type 2 vectors with a Single-Step Gravity-Flow Column," Human Gene Therapy 12:71-76 (2001).
Bagley et al., "sFLT01: A Novel Fusion Protein with Antiangiogenic Activity," Molecular Cancer Therapeutics 10:404-415 (2011).
Barleon et. al., "Protein Chemistyr and Structure: Mapping of the Sites for Ligand Binding and Receptor Dimerization at the Extracellular Domain of the Vascular Endothelial Growth Factor Receptor FLT-1," J. Biol. Chem. 272:10382-10388 (1997).
Bobo et al., "Convection-enhanced delivery of macromolecules in the brain," Proc. Natl. Acad. Sci. U.S.A. 91(6):2076-2080 (1994).
Bråkenhielm et al., "Angiogenesis Inhibitor, TNP-470, Prevents Diet-Induced and Genetic Obesity in Mice," Circulation Research 94:1579-1588 (2004).
Cunningham et al., "Identification of the Extracellular Domains of Flt-1 That Mediate Ligand Interactions," Biochem. Biophys. Res. Comm. 231:596-599 (1997).
Davidson et al., "Recombinant adeno-associated virus type 2, 4, and 5 vectors: Transduction of variant cell types and regions in the mammalian central nervous system," Proc. Natl. Acad. Sci. U.S.A. 97(7):3428-3432 (2000).
Davis-Smyth et. al., "The second immunoglobulin-like domain of the VEGF tyrosine kinase receptor Flt-1 determines ligand binding and may initiate a signal transduction cascade," EMBO J. 15:4919-4927 (1996).
Flotte et al., "Phase I trial of intramuscular injection of a recombinant adeno-associated virus alpha 1-antitrypsin (rAAV2-CB-hAAT) gene vector to AAt-deficient adults," Human Gene Therapy 15:93-128 (2004).
Grammas et al., "Microvessels from Alzheimer's Disease Brains Kill Neurons in Vitro," Am. J. Pathol. 154(2):337-342 (1999).
Healy et al., "Angiogenesis: a new theory for endometriosis," Human Reproduction Update 4:736-740 (1998).
Holash et al., "VEGF-Trap: A VEGF blocker with potent antitumor effects," Proc. Natl. Acad. Sci. U.S.A. 99:11393-11398 (2002).
Hurwitz et al., "Bevacizumab plus irinotecan, fluorouracil, and leucovorin for metastatic colorectal cancer," New Engl. J. Med. 350:2335-2342 (2004).
International Preliminary Report on Patentability issued in PCT/US2012/051412 dated Feb. 25, 2014 (6 pages).

(Continued)

*Primary Examiner* — Christine J Saoud
*Assistant Examiner* — Jon M Lockard
(74) *Attorney, Agent, or Firm* — Fish & Richardson P.C.

(57) ABSTRACT

Provided are chimeric VEGF-binding proteins and nucleic acids (e.g., a vector) encoding chimeric VEGF-binding proteins, methods and host cells for producing these proteins and nucleic acids, and pharmaceutical compositions containing these proteins and nucleic acids. Also provided are methods of treating an angiogenic disease or disorder that include administering at least one of the chimeric VEGF-binding proteins or at least one of the nucleic acids (e.g., a vector) encoding a chimeric VEGF-binding protein.

21 Claims, 8 Drawing Sheets
Specification includes a Sequence Listing.

(56) References Cited

OTHER PUBLICATIONS

International Search Report and Written Opinion issued in PCT/US2012/51412 dated Dec. 7, 2012 (8 pages).
Iruela-Arispe et al., "Inhibition of Angiogenesis by Thrombospondin-1 Is Mediated by 2 Independent Regions Within the Type 1 Repeats," Circulation 100:1423-1431 (1999).
Kisker et al., "Continuous administration of endostatin by intraperitoneally implanted osmotic pump improves the efficacy and potency of therapy in a mouse xenograft tumor model," Cancer Research 61:7669-7674 (2001).
Koch, A. E., "The role of angiogenesis in rheumatoid arthritis: recent developments," Ann. Rheum. Dis. 59(Suppl. 1):i65-i71 (2000).
Kuo et al., "Comparative evaluation of the antitumor activity of antiangiogenic proteins delivered by gene transfer," Proc. Natl. Acad. Sci. U.S.A. 98:4605-4610 (2001).
Nguyen et al., "Convection-enhanced delivery of AAV-2 combined with heparin increases TK gene transfer in the rat brain," Neuroreport 12(9):1961-1964 (2001).
Paleolog, E. M., "Angiogenesis in rheumatoid arthritis," Arthritis Res. 4(Suppl. 3), S81-S90 (2002).
Palu et al., "In pursuit of new developments for gene therapy," Journal of Biotechnology. 68:1-13 (1999).
Park et al., "Placenta Growth Factor: Potentiation of Vascular Endothelial Growth Factor Bioactivity, In Vitro and In Vivo, and High Affinity Bidning to Flt-1 But Not To Flk-1KDR," J. Biol. Chem. 269:25646-25654 (1994).
Passini et al., "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice," J. Virol. 77(12):7034-7040 (2003).
Pechan et al., "Novel anti-VEGF chimeric molecules delivered by AAV vectors for inhibition of retinal neovascularization," Gene Therapy 16:10-16 (2009).
Phillips, A.J., "The challenge of gene therapy and DNA delivery," J. Pharm. Pharmacol. 53:1169-1174 (2001).
Schultheiss et al., "In vivo characterization of endothelial cell activation in a transgenic mouse model of Alzheimer's disease," Angiogenesis 9(2):59-65 (2006).
Summerford and Samulski, "Membrain-Associated Heparan Sulfate Proteoglycan Is a Receptor for Adeno-Associated Virus Type 2 Virions," J. Virol. 72:1438-1445 (1998).
Summerford and Samulski, "Viral receptors and vector purification: New approaches for generating clinical-grade reagents," Nat. Med. 5:587-588 (1999).
Tjin Tham Sjin et al., "A 27-amino-acid synthetic peptide corresponding to the NH2-terminal zinc-binding domain of endostatin is responsible for its antitumor activity," Cancer Res. 65:3656-3663.
Wiesmann et al., "Crystal Structure at 1.7 Å Resolution of VEGF in Complex with Domain 2 of the Flt-1 Receptor," Cell 91:695-704 (1997).
Baffert et al., "Cellular changes in normal blood capillaries undergoing regression after inhibition of VEGF signaling," Am. J. Physiol. Heart Circ. Physiol. 290:H547-H559 (2006).
Tam et al., "VEGF modulates erythropoiesis through regulation of adult hepatic erythropoietin synthesis," Nature Med. 12(7):793-800 (2006).
European Search Report issued in EP12826108.8 dated May 20, 2015 (4 pages).
Communication issued in European Patent Appl. No. 12826108.8, mailed on Jun. 2, 2015 (5 pages).
Communication issued in European Patent Appl. No. 12826108.8, mailed on Feb. 24, 2016 (4 pages).

* cited by examiner

Figure 1. Structure of Vegf-Trap 1 and Vegf-Trap 3

VEGF-BINDING PROTEIN FOR BLOCKADE OF ANGIOGENESIS

CROSS-REFERENCE TO RELATED APPLICATION

This application is a continuation application of U.S. patent application Ser. No. 14/239,687, filed on Feb. 19, 2014 (issued as U.S. Pat. No. 9,701,731), which is a U.S. National Stage application under 35 U.S.C. § 371 of International Patent Application No. PCT/US2012/051412, filed on Aug. 17, 2012, which claims priority to U.S. Patent Application Ser. No. 61/525,278, filed on Aug. 19, 2011, the entire contents of which are hereby incorporated by reference.

FIELD OF INVENTION

The present invention is related to the treatment of angiogenesis-related diseases and disorders.

BACKGROUND OF INVENTION

Vascular endothelial growth factor (VEGF) is an endothelial cell-specific mitogenic and angiogenic inducer that mediates its effect through at least two high affinity-binding receptor tyrosine kinases, Flt-1 and KDR, which are expressed only on the surface of vascular endothelial cells. Flt-1 is required for endothelial cell morphorgenesis whereas KDR is involved primarily with mitogenesis. Gene knockout studies have shown that both Flt-1 and KDR are essential for the normal development of the mammalian vascular system despite their distinct respective roles in endothelial cell proliferation and differentiation. Both Flt-1 and KDR tyrosine kinase receptors have seven immunoglobulin-like (Ig-like) domains which form the extracellular ligand-binding regions of the receptors, a transmembrane domain, and an intracellular catalytic tyrosine kinase domain.

VEGF plays a critical role during normal embryonic angiogenesis and also in the pathological development of new blood vessels in a number of diseases including cancer and in aberrant angiogenesis such as hemangiomas. Solid tumors use blood vessels to obtain oxygen and nutrients and to remove waste materials. In addition these tumors produce stromal factors that induce the formation of new blood vessels to support the tumors' continued growth. Therefore an anti-angiogenic approach represents an attractive and feasible cancer therapeutic option, for example, by inhibiting the VEGF signaling pathway.

One strategy of blocking the VEGF signaling pathway is to sequester away circulating serum VEGF using VEGF binding proteins. VEGF binding proteins serve as decoy receptors working to reduce the amount of circulating VEGF ligand. VEGF binding proteins include e.g., humanized monoclonal antibodies, soluble VEGF receptors, or chimeric VEGF-trap molecules. Chimeric VEGF traps containing anywhere from two to seven of the extracellular Ig-like domains in various combinations have been described (Holash J. et al. Proc. Natl. Acad. Sci. USA 2002, 99:11393-98; Davis-Smyth T. et. al. EMBO 1996, 15:4919-4927; U.S. Pat. No. 6,100,071; U.S. Pat. No. 7,087,411), these VEGF-traps are not optimally effective because they vary in their molecular sizes, VEGF-binding affinity, anti-tumor activity, and pharmacokinetics in vivo. These VEGF-traps are currently administered systemically, and multiple administrations are required in order to maintain a sustained delivery for the VEGF-traps to be therapeutically effective. A gene-therapy approach for sustained delivery of VEGF-traps has been attempted using adenoviruses but the method has been hampered by tissue toxicity issues and low expression of the transgene.

SUMMARY OF THE INVENTION

Embodiments of the present invention are based on the discovery that a chimeric protein comprising a single immunoglobulin-like domain (Ig-like) derived from the vascular endothelial growth factor receptor tyrosine kinase Flt-1 and the fragment crystallizable (Fc) constant region of an immunoglobulin has potent anti-tumor activity in multiple tumor models. Such chimeric VEGF-binding protein effectively inhibits tumor growth in vivo. In a particular embodiment, the chimeric VEGF-binding protein can be effectively delivered via intramuscular injection of adeno-associated virus expressing the protein.

In one aspect, a chimeric VEGF-binding protein comprising a first portion and second portion is provided. In one embodiment of this aspect, the first portion can consist of, for example, amino acids 129-231 of the flt-1 tyrosine kinase receptor (Genbank Accession No.: BC039007, SEQ ID NO: 1), while the second portion comprises an Fc region of immunoglobulin G1 (e.g., amino acids 247-473 of Genbank accession # BC092518 or amino acids 243-469 of SEQ ID NO: 2).

In another embodiment, the chimeric VEGF-binding protein can further comprise a signal peptide, including, but not limited to the signal peptide of the flt-1 tyrosine kinase receptor (SEQ ID NO:5).

In another embodiment, the Fc region of immunoglobulin G1 carried by the chimeric polypeptide is a human Fc region of immunoglobulin G1. For example, the Fc region of immunoglobulin G1 can comprise or consist of amino acids 247-473 of IgG1 (Genbank Accession No.: BC092518). In another example, the Fc region of immunoglobulin G1 can comprise or consist of amino acids 243-469 of SEQ ID NO: 2.

In another embodiment, the Fc region can comprise a reduced immunogenic derivative of an Fc region of immunoglobulin G1.

In another aspect, the invention provides a pharmaceutical composition comprising a chimeric VEGF-binding protein of the first aspect and a pharmaceutically acceptable carrier.

In another aspect, the invention provides an isolated polynucleotide encoding a chimeric VEGF-binding protein of the first aspect. In one embodiment, the polynucleotide can be in the form of a recombinant vector comprising the polynucleotide encoding a chimeric VEGF-binding protein of the first aspect. In another embodiment, the recombinant vector can be an expression vector that is, e.g., compatible with a protein expression system using host cells including mammalian cells, insect cells, yeast cells, bacterial cells and plant cells. The invention also provides a host cell comprising such a recombinant expression vector. In one embodiment, the vector is a viral vector, including, but not limited to an adeno-associated virus (AAV) vector or a lentivial vector.

In another aspect, provided are methods of treating an angiogenic disease or disorder, the methods comprising administering to a subject in need thereof a vector comprising an isolated polynucleotide encoding a chimeric VEGF-binding protein of the first aspect or administering a pharmaceutical composition comprising a chimeric VEGF-binding protein of the first aspect and a pharmaceutically acceptable carrier.

In one embodiment of this aspect, provided are methods of treating an angiogenic disease or disorder, the methods comprising administering to a subject in need thereof a pharmaceutical composition comprising a chimeric VEGF-binding protein, wherein the chimeric VEGF-binding protein comprises an immunoglobulin-like domain 2 of a vascular endothelial growth factor receptor and an Fc region of immunoglobulin G1 or a reduced immunogenic derivative of such an Fc region. Also provided are methods of using a chimeric VEGF-binding protein comprising an immunoglobulin-like domain 2 of a vascular endothelial growth factor receptor and an Fc region of immunoglobulin G1 or a reduced immunogenic derivative of such an Fc region in the manufacture for treating an angiogenic disease or disorder in a subject. Also provided are chimeric VEGF-binding proteins comprising an immunoglobulin-like domain 2 of a vascular endothelial growth factor receptor and an Fc region of immunoglobulin G1 or a reduced immunogenic derivative of such an Fc region for use in treating an angiogenic disease or disorder in a subject.

In another aspect, provided are methods of producing a chimeric VEGF-binding protein of the first aspect, the methods comprising introducing a recombinant vector encoding such chimeric VEGF-binding protein to an isolated host cell, growing or maintaining the cell under conditions permitting the production of the chimeric protein, and recovering the chimeric protein so produced.

In one embodiment of the treatment methods described herein, a method of treating cancer is provided, wherein said cancer can be selected, for example, from the group consisting of glioma, bladder cancer, breast cancer, colon cancer, melanoma, liver cancer, lung cancer, ovarian cancer, prostate cancer, renal cell carcinoma, hemangioma and astrocytoma.

In another embodiment of the treatment methods described herein, methods of treating age-related macular degeneration, wet macular degeneration, and diabetic retinopathy are provided.

DETAILED DESCRIPTION OF THE INVENTION

Definitions

Figure 1:
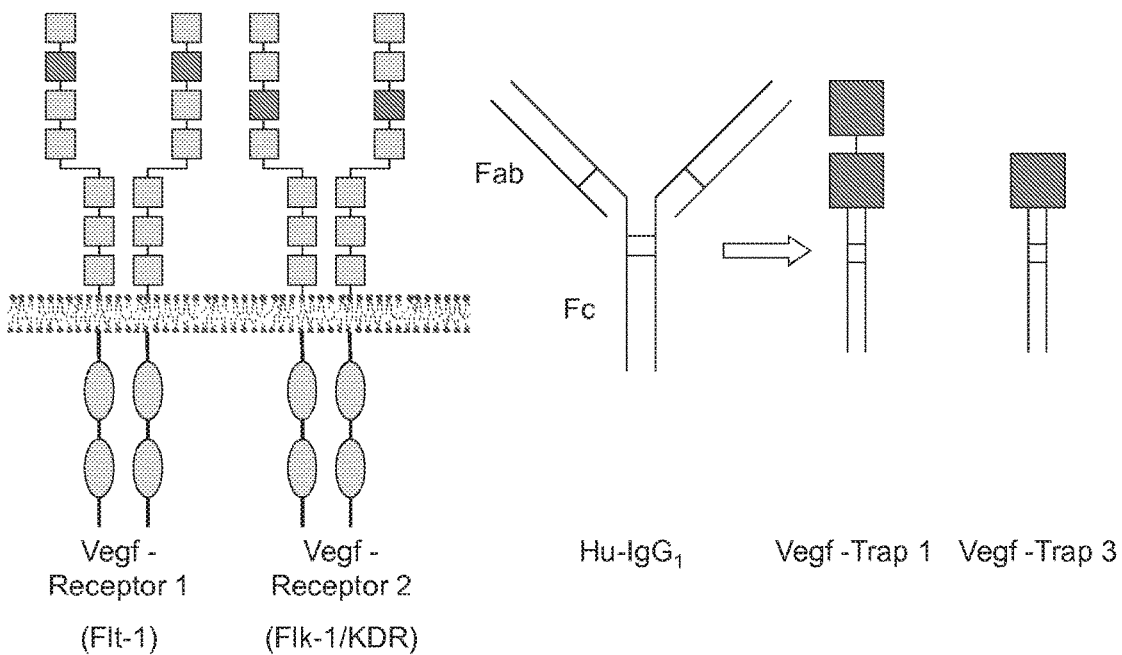
FIG. 1. Construction of a modified VEGF-Trap protein for gene therapy applications. Vegf-Trap 1 (VT1) was constructed as described by Holash et al. (1). Vegf-Trap 3 (VT3) was similarly constructed by attaching the second Ig-like domain of Flt-1 to Fc-huIgG$_1$. The final construct encodes the signal sequence of VEGF-receptor 1 (Amino acids 1-26 of Genbank accession # BC039007) (SEQ. ID. No. 1), the second Ig-like domain (Amino acids 129-231 of Genbank accession # BC039007) (SEQ. ID. No. 1) fused directly to the huIgG1 (amino acids 247-473 of Genbank accession # BC092518).

As used herein, the term "chimeric VEGF-binding protein" refers to a protein comprising a first portion, the first portion consisting of sections of the Ig-like domains the tyrosine kinase receptor Flt-1, and a second portion comprising a Fc region of immunoglobulin G1 or a reduced immunogenic derivative of a Fc region of immunoglobulin G1. The terms "chimeric VEGF-binding protein", "VEGF-binding protein" and "VEGF Trap" protein are used interchangeably here. A chimeric VEGF-binding protein of this type can specifically bind VEGF as measured in an assay as described herein.

As used herein, the term "chimeric" describes being composed of parts of different protein or DNA from different origins. For example, a chimeric VEGF-binding protein is composed of the Ig-like domain 2 from the Flt-1 protein and the Fc region of an immunoglobulin protein. Similarly a chimeric polynucleotide is composed of a DNA fragment encoding the Ig-like domain 2 of the Flt-1 protein and a DNA fragment encoding the Fc region of an immunoglobulin protein.

As used herein, the term "Fc region" refers to the fragment crystallizable region (Fc region) of an antibody that contributes the constant domains of an immunoglobulin.

As used herein, the term "reduced immunogenic derivative of an Fc region" refers to an Fc region that contains certain point mutations that render the Fc region less likely to activate and elicit an immune response to the altered Fc region by reducing the ability to bind with the FcRγ1 receptor on B and T cells. A "reduced immunogenic derivative of an Fc region" triggers less than 70% of the immune system response of a wild-type Fc region, and preferably less than 50%, 40%, 20%, 10% or lower relative to wild-type Fc.

The term "vector", as used herein, refers to a nucleic acid construct designed for delivery to a host cell or transfer between different host cells. As used herein, a vector may be viral or non-viral.

As used herein, the term "expression vector" refers to a vector that has the ability to incorporate and express heterologous DNA fragments in a cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the coding sequence for a VEGF-binding protein in place of non-essential viral genes. The vector and/or particle may be utilized for the purpose of transferring DNA, RNA or other nucleic acids into cells either in vitro or in vivo. Numerous forms of viral vectors are known in the art.

The term "replication incompetent" as used herein means the viral vector cannot further replicate and package its genomes. For example, when the cells of a subject are infected with replication incompetent recombinant adeno-associated virus (rAAV) virions, the heterologous (also known as transgene) gene is expressed in the patient's cells, but, the rAAV is replication defective (e.g., lacks accessory genes that encode essential proteins from packaging the virus) and viral particles cannot be formed in the patient's cells.

The term "gene" or "coding sequence" means the nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

The term "recombinant" as used herein with reference to nucleic acid molecules refers to a combination of nucleic acid molecules that are joined together using recombinant DNA technology into a progeny nucleic acid molecule. As used herein with reference to viruses, cells, and organisms, the terms "recombinant," "transformed," and "transgenic" refer to a host virus, cell, or organism into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Recombinant viruses, cells, and organisms are understood to encompass not only the end product of a transformation process, but also recombinant progeny thereof. A "non-transformed," "non-transgenic," or "non-recombinant" host refers to a wildtype virus, cell, or organism that does not contain the heterologous nucleic acid molecule.

The term "angiogenesis", as used herein refers to the sprouting of blood vessels from pre-existing blood vessels, characterized by endothelial cell proliferation and the proliferation and migration of tube forming cells. Angiogenesis can be triggered by certain pathological conditions, such as the growth of solid tumors and metastasis.

As used herein, the term "angiogenic disease or disorder" refers to diseases or disorders that are the direct result of aberrant blood vessel proliferation (e.g. diabetic retinopathy). The term also refer to disease or disorder whose pathological progression is dependent on a good blood supply and thus blood vessel proliferation. The term "angiogenesis-related disease or disorder" and "angiogenic disease or disorder" are used interchangeably herein.

As used herein, the term "variant" refers to the chimeric VEGF-binding protein with one or more amino acid changes to the amino acid sequence of the polypeptide that retains both VEGF-binding activity and anti-angiogenic activity. Thus the polypeptide sequence of a variant chimeric VEGF-binding polypeptide varies from that of, e.g., a construct of SEQ. ID. No. 3.

Chimeric VEGF-Binding Protein

Embodiments of the invention are directed to chimeric VEGF-binding proteins. Chimeric VEGF-binding proteins as described herein are comprised of two portions: the first portion consisting of amino acids 129-231 of the Flt-1 tyrosine kinase receptor (Genbank Accession No. BC039007) (SEQ ID NO: 1), and a second portion comprising a Fc region of human immunoglobulin G1. In non-limiting embodiments, the second portion comprising the Fc region can include amino acids 247-473 of IgG1 (Genbank Accession No. BC092518) or amino acids 243-469 of SEQ ID NO: 2.

The amino acid sequence of one such chimeric VEGF-binding protein, also referred to herein as VEGF-Trap 3 or VT3, is:

```
                                        (SEQ. ID. NO. 3)
MVSYWDTGVLLCALLSCLLLTGSSSGSDTGRPFVEMYSEIPEIIHMTEG

RELVIPCRVTSPNITVTLKKFPLDTLIPDGKRIIWDSRKGFIISNATYK

EIGLLTCEATVNGHLYKTNYLTHRQTNTIIDDKTHTCPPCPAPELLGGP

SVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHN

HYTQKSLSLSPGK.
```

The extracellular regions of the VEGF tyrosine kinase receptors Flt-1 and KDR are responsible for binding the ligand VEGF. The extracellular region has seven immunoglobulin-like (Ig-like) domains. The ligand binding function resides within the first three domains (Davis-Smyth T. et. al., 1996, J EMBO 15: 4919-4927; Barleon et. al., 1997, J. Biol. Chem. 272:10382-88; Cunningham et. al., 1997, Biochem. Biophys. Res. Comm. 231: 596-599; Wiesmann C. et. al., 1997, Cell 91:695-704). Of these seven Ig-like domains, it has been shown that the Ig-like domain 2 is essential for binding ligand VEGF, although the Ig-like domain 2 (amino acids 134-226) alone was not sufficient for VEGF binding in vitro (Davis-Smyth T. et. al., 1996, J EMBO 15: 4919-4927). As described herein, surprisingly, a region of the Ig-like domain 2 of Flt-1(amino acids 129-231) is essential and sufficient for binding VEGF ligand in vitro. This Ig-like domain 2 functions effectively in suppressing tumor growth in vivo. Since the two high affinity receptor tyrosine kinases, Flt-1 and KDR, share a high degree of sequence similarity and identity, the Ig-like domains 2 of Flt-1 and KDR are interchangeable. Therefore, in one embodiment, the invention encompasses a chimeric VEGF-binding protein comprising the Ig-like domain 2 of KDR (amino acids 122-286 of KDR, genbank Accession No.: NM002253, SEQ. ID. No. 6).

In one embodiment, a chimeric VEGF-binding protein comprises a first portion, the first portion consisting of amino acids 129-231 of the Flt-1 tyrosine kinase receptor (SEQ ID No.: 1), and a second portion comprising an Fc region of immunoglobulin G1 or a reduced immunogenic derivative of an Fc region of immunoglobulin G1. The Fc portion of an immunoglobulin has a long plasma half-life (Capon, et. al., 1989, Nature 337: 525-531). The fusion of the single Ig-like domain 2 from either Flt-1 or KDR to the Fc portion of an immunoglobulin will serve to improve the plasma half-life and pharmacokinetics of the VEGF-binding IgG domain 2 in vivo.

Previously Fc-chimeric proteins have been to shown to elicit an inflammatory response upon long term usage or at high dosage, and especially when the Fc-chimera is used therapeutically and the Fc region is derived from a heterologous source different from the animal recipient of the Fc-chimeric protein. In one embodiment, the Fc region of immunoglobulin used in the chimeric VEGF-binding protein is a reduced immunogenic derivative of a Fc region of IgG and is derived from a human. The reduced immunogenic activity results from a reduced affinity for the Fc receptors on B and T cells. The Fc regions of immunoglobulin G subtype 4 (IgG4) and IgG2 have 10-fold lower affinity and no affinity for the FcRγ1 receptor respectively. In one embodiment, the Fc region of IgG4 and IgG2 is used in the construction of chimeric VEGF-binding protein. In another embodiment, the Fc region has certain point mutations which further reduces its affinity to the FcRγ1 receptor or that enhances the serum half-life of the Fc-fusion molecule. For example, a serine to proline mutation in residue 241 (kabat numbering) in IgG4 results in increased serum half-life of IgG4 (Angal S., et al., 1993, Mol. Immuno. 130:105-108). A substitution of leucine for glutamate at residue 248 (kabat numbering) in IgG2b decreases the affinity for the FcRγ1 receptor (Canfield and Morrison, J Exp Med. 1991 Jun. 1; 173(6):1483-91).

In another embodiment, the chimeric VEGF-binding protein has amino acid point mutations and/or substitutions within the Ig-like domain 2 that enhance the binding affinity of the chimeric VEGF-binding protein for the homodimeric VEGF ligand. Examples of such mutations include a substitution of Glu 201 with Asp, Leu 205 with tyrosine, tryptophan replacing Leu 169 on strand βc (Wiesmann C. et. al., 1997, Cell 91:695-704), and replacing Tyr-220 and Arg-224 with hydrophobic amino acids such as isoleucine and phenylalanine. In one embodiment, variant forms of chimeric VEGF-binding protein may have more than one mutation. In another embodiment, random or systematic mutagenesis can be performed to create a library of variant forms of VEGF-binding protein to screen for variant forms with greater VEGF-binding. In vitro binding assays which can be performed routinely to determine if a particular mutation in the Ig-like domain 2 affects VEGF ligand binding ability are described by Park el. al. (J. Biol. Chem. 1994, 269:25646-54) and Holash J. et al. (Proc. Natl. Acad. Sci. USA 2002, 99:11393-98) which are incorporated by reference herein. A greater binding affinity as the term is used herein refers to a 5% or greater decrease in $K_d$ relative to wild-type binding to VEGF.

In one embodiment, a chimeric VEGF-binding protein comprises a signal peptide at the N-terminus. This signal peptide is a short (3-60 amino acids long) peptide chain that directs the post-translational transport of a protein. For the current invention, the signal peptide should guide the DNA sequence encoding the chimeric VEGF-binding protein for co-translation in the endoplasmic reticulum and subsequent secretion of the translated protein. In one embodiment, the signal peptide is the signal peptide H$_2$N-Met-Met-Ser-Phe-Val-Ser-Leu-Leu-Val-Gly-Ile-Leu-Phe-Trp-Ala-Thr-Glu-Ala-Glu-Gln-Leu-Thr-Lys-Cys-Glu-Val-Phe-Gln (SEQ. ID. No.: 4). In one embodiment, the chimeric VEGF-binding protein comprises a signal peptide of the Flt-1 tyrosine kinase receptor (SEQ. ID. No.: 1), amino acids 1-26, Met-Val-Ser-Tyr-Trp-Asp-Thr-Gly-Val-Leu-Leu-Cys-Ala-Leu-Leu-Ser-Cys-Leu-Leu-Leu-Thr-Gly-Ser-Ser-Ser-Gly-Ser (SEQ. ID. No. 5). In another embodiment, the signal peptide is that of the KDR tyrosine kinase receptor (Genbank Accession No. NM_002253) (SEQ. ID. No. 6), amino acids 1-26, Met-Gln-Ser-Lys-Val-Leu-Leu-Ala-Val-Ala-Leu-Trp-Leu-Cys-Val-Glu-Thr-Arg-Ala-Ala-Ser-Val-Gly-Leu-Pro-Ser (SEQ. ID. No. 7). In a preferred example, a chimeric VEGF-binding protein, as described herein, can have the following protein fragments arranged in the amino to carboxyl terminus orientation in the polypeptide: the signal peptide (amino acids 1-26) the followed by the Ig-like domain 2 (amino acids 129-231) of Flt-1 tyrosine kinase receptor, and ending with the Fc region (amino acids 247-473) of human IgG1.

Synthesis of Isolated Chimeric DNA Coding Sequence for a Chimeric VEGF-Binding Protein Unless otherwise indicated, all technical and scientific terms used herein have the same meaning as they would to one skilled in the art of the present invention. Further, unless otherwise required by context, singular terms shall include pluralities and plural terms shall include the singular.

The process of engineering the chimeric protein, the coding DNA sequence, expression vectors, viral vectors, and expression purification of the invention can be performed by conventional recombinant molecular biology and protein biochemistry techniques such as those described in Maniatis et al. (Molecular Cloning—A Laboratory Manual; Cold Spring Harbor, 1982) and DNA Cloning Vols I, II, and III (D. Glover ed., IRL Press Ltd.), Sambrook et al., (1989, Molecular Cloning, A Laboratory Manual; Cold Spring Harbor Laboratory Press, NY, USA), Current Protocols in Molecular Biology (CPMB) (Fred M. Ausubel et al. ed., John Wiley and Sons, Inc.) and Current Protocols in Protein Science (CPPS) (John E. Coligan, et al., ed., John Wiley and Sons, Inc.).

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

Conventional polymerase chain reaction (PCR) cloning techniques can be used to generate an isolated chimeric DNA sequence encoding the chimeric VEGF-binding protein. A chimeric DNA sequence is cloned into a general purpose cloning vector such as pUC19, pBR322, pBluescript vectors (Stratagene Inc.) or pCR TOPO® from Invitrogen Inc. The resultant recombinant vector carrying the isolated chimeric DNA sequence encoding a chimeric VEGF-binding protein can then be used for further molecular biological manipulations such as site-directed mutagenesis to enhance VEGF-binding and/or to reduce the immunogenic properties of the chimeric protein, or can be subcloned into protein expression vectors or viral vectors for protein synthesis in a variety of protein expression systems using host cells selected from the group consisting of mammalian cell lines, insect cell lines, yeast, bacteria, and plant cells.

Embodied herein is an isolated polynucleotide encoding a chimeric VEGF-binding protein comprising a first portion, the first portion consisting of amino acids 129-231 of the Flt-1 tyrosine kinase receptor (SEQ ID No.: 1), and a second portion comprising a Fc region of immunoglobulin G1 or a reduced immunogenic derivative of a Fc region of immunoglobulin G1. The single isolated DNA encoding the chimeric VEGF-binding protein is made three up of separate DNA fragments, each fragment coding for an individual part of the chimeric protein: the signal peptide, the Ig-like domain 2 of Flt-1, and the Fc region of an IgG. Three pairs of specific PCR oligonucleotide primers can be used to PCR amplify the three separate DNA fragments corresponding to the amino acids 1-26 and 129-231 of the Flt-1 tyrosine kinase receptor (Genbank accession # BC039007) (SEQ ID No.: 1), and the amino acids 247-473 of human IgG1 (Genbank accession # BC092518). Each PCR primer should have at least 15 nucleotides overlapping with its corresponding templates at the region to be amplified. The polymerase used in the PCR amplification should have high fidelity such as Strategene's PfuUltra™ polymerase for reducing sequence mistakes during the PCR amplification process. For ease of ligating the three separate PCR fragments together and then inserting into a cloning vector, the PCR primers should also have distinct and unique restriction digestion sites on their flanking ends that do not anneal to the DNA template during PCR amplification. The choice of the restriction digestion sites for each pair of specific primers should be such that the open reading frame of the chimeric DNA sequence is in-frame and will encode the predicted chimeric VEGF-binding protein from beginning to end with no stop codons. At the same time the chosen restriction digestion sites should not be found within the DNA coding sequences corresponding to the amino acids 1-26 and 129-231 of the Flt-1 tyrosine kinase receptor (SEQ. ID. No.:1), and the amino acids 247-473 of human IgG1 (Genbank accession # BC092518). Conventional restriction digestion and ligation techniques can be used to insert the chimeric DNA coding sequence into a cloning vector. Alternatively the chimeric DNA can be ligated into a vector using the TOPO® cloning method in Invitrogen topoisomerase-assisted TA vectors such as pCR®-TOPO, pCR®-Blunt II-TOPO, pENTR/D-TOPO®, and pENTR/SD/D-TOPO®. Both pENTR/D-TOPO®, and pENTR/SD/D-TOPO® are directional TOPO entry vectors which allow the cloning of the chimeric VEGF DNA sequence in the 5'→3' orientation into a Gateway® expression vector. Directional cloning in the 5'→3' orientation facilitate the unidirection insertion of the chimeric VEGF DNA sequence into a protein expression vector such that the promoter is upstream of the 5' ATG start codon of the chimeric VEGF DNA sequence, enabling promoter driven protein expression. The recombinant vector carrying the chimeric VEGF DNA sequence can be transfected into and propagated in general cloning E. coli such as XL1 Blue, SURE (Stratagene) and TOP-10 cells (Invitrogen).

In one embodiment, the invention provides an isolated polynucleotide encoding a chimeric VEGF-binding protein. An example of such an isolated polynucleotide is:

(SEQ. ID. No. 8)
```
5'-
Atggtgagctactgggacactggggtgctgctgtgtgccctgctgagctg
cctgctgctgactggcagcagctctggctctgacactggcaggcccatgt
ggagatgtactctgagatccctgagatcatccacatgactgagggcaggg
agctggtgatccctgcagagtgaccagcccaacatcactgtgaccctg
aagaagttcccctggacaccctgatccctgatggcaagaggatcatctg
ggacagcaggaagggcttcatcatcagcaatgccacctacaaggagattg
gcctgctgacctgtgaggccactgtgaatggccacctgtacaagaccaac
tacctgacccacaggcagaccaacaccatcatcgatgacaaaactcacac
atgcccaccgtgcccagcacctgaactcctgggggaccgtcagtcttcc
tcttccccccaaaacccaaggacaccctcatgatctcccggacccctgag
gtcacatgcgtggtggtggacgtgagccacgaagaccctgaggtcaagtt
caactggtacgtggacggcgtggaggtgcataatgccaagacaaagccgc
gggaggagcagtacaacagcacgtaccgtgtggtcagcgtcctcaccgtc
ctgcaccaggactggctgaatggcaaggagtacaagtgcaaggtctccaa
caaagccctcccagcccccatcgagaaaaccatctccaaagccaaagggc
agccccgagagccacaggtgtacaccctgcccccatcccgggatgagctg
accaagaaccaggtcagcctgacctgcctggtcaaaggcttctatcccag
cgacatcgccgtggagtgggagagtatgggcagccggagaacaactacaa
gaccacgcacccgtgaggactccgacggctcatcacctctacagcaagct
caccgtggacaagagcaggtggcagcaggggaacgtcttctcatgctccg
tgatgcatgaggctctgcacaaccactacacgcagaagagcctctccctg
taccgggtaaatga-3'.
```

Specific site-directed mutagenesis of the chimeric VEGF DNA sequence in a vector can be used to create specific amino acid mutations and substitutions at the Fc portion to further reduce the immunogenic properties of eventual chimeric VEGF-binding protein. By the same token, site-directed mutagenesis can be carried out in the Ig-like domain 2 to enhance the VEGF-binding affinity of the chimeric VEGF-binding protein. Examples of amino acid mutations are serine to proline mutation and a substitution of leucine for glutamate in the Fc-region. Site-directed mutagenesis may be carried out using the QuikChange® site-directed mutagenesis kit from Stratagene according to manufacture's instructions or any methods known in the art.

Expression Vectors and Expression Systems for Expression of Chimeric VEGF-Binding Protein In one embodiment, the invention provides for expression vectors carrying a polynucleotide that encodes a chimeric VEGF-binding protein for the expression and purification of the recombinant chimeric VEGF-binding protein produced from a protein expression system using host cells selected from, e.g., mammalian, insect, yeast, bacterial, or plant cells.

In one embodiment, the recombinant vector that expresses a chimeric VEGF-binding protein is a viral vector. The viral vector can be any viral vector known in the art including but not limited to those derived from adenovirus, adeno-associated virus (AAV), retrovirus, and lentivirus. Recombinant viruses provide a versatile system for gene expression studies and therapeutic applications.

In another embodiment, the invention provides for a host cell comprising a expression vector which expresses the chimeric VEGF-binding protein. The expression host cell may be derived from any of a number of sources, e.g., bacteria, such as *E. coli*, yeasts, mammals, insects, and plant cells such as *chymadomonas*. In another embodiment, the recombinant chimeric VEGF-binding protein can be produced from expression vectors suitable for cell-free expression systems. From the cloning vector, the chimeric VEGF DNA sequence can be subcloned into a recombinant expression vector that is appropriate for the expression of the chimeric VEGF-binding protein in mammalian, insect, yeast, bacterial, or plant cells or a cell-free expression system such as a rabbit reticulocyte expression system. Subcloning can be achieved by PCR cloning, restriction digestion followed by ligation, or recombination reaction such as those of the lambda phage-based site-specific recombination using the Gateway® LR and BP Clonase™ enzyme mixtures. Subcloning should be unidirectional such that the 5' ATG start codon of the chimeric VEGF DNA sequence is downstream of the promoter in the expression vector. Alternatively, when the chimeric VEGF DNA sequence is cloned into pENTR/D-TOPO®, pENTR/SD/D-TOPO® (directional entry vectors), or any of the Invitrogen's Gateway® Technology pENTR (entry) vectors, the chimeric VEGF DNA sequence can be transferred into the various Gateways expression vectors (destination) for protein expression in mammalian cells, *E. coli*, insects and yeast respectively in one single recombination reaction. Some of the Gateway® destination vectors are designed for the constructions of baculovirus, adenovirus, adeno-associated virus (AAV), retrovirus, and lentiviruses, which upon infecting their respective host cells, permit heterologous expression of the chimeric VEGF-binding protein in the host cells. The Gateway® Technology uses lambda phage-based site-specific recombination instead of restriction endonuclease and ligase to insert a gene of interest into an expression vector. The DNA recombination sequences (attL, attR, attB, and attP) and the LR and BP Clonase™ enzyme mixtures that mediate the lambda recombination reactions are the foundation of Gateway® Technology. Transferring a gene into a destination vector is accomplished in just two steps: Step 1: Clone the chimeric DNA sequence into an entry vector such as pENTR/D-TOPO®. Step 2: Mix the entry clone containing the chimeric DNA sequence in vitro with the appropriate Gateway® expression vector (destination vector) and Gateway® LR Clonase™ enzyme mix. There are Gateway® expression vectors for protein expression in *E. coli*, insect cells, mammalian cells, and yeast. Site-specific recombination between the art sites (attR×attL and attB×attP) generates an expression vector and a by-product. The expression vector contains the chimeric DNA sequence recombined into the destination vector backbone. Following transformation and selection in *E. coli*, the expression vector is ready to be used for expression in the appropriate host.

The expression vector should have the necessary 5' upstream and 3' downstream regulatory elements such as promoter sequences, ribosome recognition and binding TATA box, and 3' UTR AAUAAA transcription termination sequence for the efficient gene transcription and translation in its respective host cell. The expression vector may have additional sequence such as 6×-histidine, V5, thioredoxin, glutathione-S-transferase, c-Myc, VSV-G, HSV, FLAG, maltose binding peptide, metal-binding peptide, HA and "secretion" signals (Honeybee melittin, α-factor, PHO, Bip), which are incorporated into the expressed recombinant chimeric VEGF-binding protein. In addition, there may be enzyme digestion sites incorporated after these sequences to facilitate enzymatic removal of them after they are not needed. These additional sequences are useful for the detection of the chimeric VEGF-binding protein expression, for protein purification by affinity chromatography, enhanced solubility of the recombinant protein in the host cytoplasm, and/or for secreting the expressed recombinant chimeric VEGF-binding protein out into the culture media, into the periplasm of the prokaryote bacteria, or the spheroplast of the yeast cells. The expression of the recombinant chimeric VEGF-binding protein can be constitutive in the host cells or it can be induced, e.g., with copper sulfate, sugars such as galactose, methanol, methylamine, thiamine, tetracycline, infection with baculovirus, and (isopropyl-beta-D-thiogalactopyranoside) IPTG, a stable synthetic analog of lactose.

Examples of expression vectors and host cells are the pET vectors (Novagen), pGEX vectors (Amersham Pharmacia), and pMAL vectors (New England labs. Inc.) for protein expression in *E. coli* host cell such as BL21, BL21(DE3) and AD494(DE3)pLysS, Rosetta (DE3), and Origami(DE3) (Novagen); the strong CMV promoter-based pcDNA3.1 (Invitrogen) and pCIneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech), pAd/CMV/V5-DEST, pAd-DEST vector (Invitrogen) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4V5-DEST™, pLenti6/V5-DEST™, and pLenti6.2/V5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFastBac™-HT (Invitrogen) for the expression in *Spodopera frugiperda* 9 (S9) and Sfl1 insect cell lines; pMT/BiP/V5-His (Invitrogen) for the expression in *Drosophila* Schneider S2 cells; *Pichia* expression vectors pPICZα, pPICZ, pFLDα and pFLD (Invitrogen) for expression in *Pichia pastoris* and vectors pMETα and pMET for expression in *P. methanolica*; pYES2/GS and pYD1 (Invitrogen) vectors for expression in yeast *Saccharomyces cerevisiae*. Recent advances in the large scale expression heterologous proteins in *Chlamydomonas reinhardtii* are described by Griesbeck C. et. al. 2006 Mol. Biotechnol. 34:213-33 and Fuhrmann M. 2004, Methods Mol Med. 94:191-5. Foreign heterologous coding sequences are inserted into the genome of the nucleus, chloroplast and mitochodria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. Biolistic gene gun method is used to introduced the vector in the algae. Upon its entry into chloroplasts, the foreign DNA is released from the gene gun particles and integrates into the chloroplast genome through homologous recombination.

A simplified system for generating recombinant adenoviruses is presented by He TC. et. al. Proc. Natl. Acad. Sci. USA 95:2509-2514, 1998. The gene of interest is first cloned into a shuttle vector, e.g. pAdTrack-CMV. The resultant plasmid is linearized by digesting with restriction endonuclease Pme I, and subsequently cotransformed into *E. coli*.

BJ5183 cells with an adenoviral backbone plasmid, e.g. pAdEasy-1 of Stratagene's AdEasy™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells(E1-transformed human embryonic kidney cells) or 911 (E1-transformed human embryonic retinal cells) (Human Gene Therapy 7:215-222, 1996). Recombinant adenovirus are generated within the HEK 293 cells.

In one embodiment, the invention provides a recombinant lentivirus for the delivery and expression of a chimeric VEGF-binding protein in either dividing and non-dividing mammalian cells. The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with ViraPower™ Lentiviral Expression systems from Invitrogen.

In one embodiment, the invention provides a recombinant adeno-associated virus (rAAV) vector for the expression of a chimeric VEGF-binding protein. In one embodiment, the rAAV vector encoding a chimeric VEGF-binding protein is administered to slow, inhibit, or prevent the growth of cancer and tumors such as glioma. Using rAAV vectors, genes can be delivered into a wide range of host cells including many different human and non-human cell lines or tissues. Because AAV is non-pathogenic and does not illicit an immune response, a multitude of pre-clinical studies have reported excellent safety profiles. rAAVs are capable of transducing a broad range of cell types and transduction is not dependent on active host cell division. High titers, >$10^8$ viral particle/ml, are easily obtained in the supernatant and $10^{11}$-$10^{12}$ viral particle/ml with further concentration. The transgene is integrated into the host genome so expression is long term and stable.

The use of alternative AAV serotypes other than AAV-2 (Davidson et al (2000), PNAS 97(7)3428-32; Passini et al (2003), J. Virol 77(12):7034-40) has demonstrated different cell tropisms and increased transduction capabilities. With respect to brain cancers, the development of novel injection techniques into the brain, specifically convection enhanced delivery (CED; Bobo et al (1994), PNAS 91(6):2076-80; Nguyen et al (2001), Neuroreport 12(9): 1961-4), has significantly enhanced the ability to transduce large areas of the brain with an AAV vector.

Large scale preparation of AAV vectors is made by a three-plasmid cotransfection of a packaging cell line: AAV vector carrying the chimeric DNA coding sequence, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12; 71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

Expression and Purification

In one embodiment, the invention provides a method of producing chimeric VEGF-binding protein comprising introducing the recombinant vector that expressed the chimeric VEGF-binding protein into an isolated host cell, growing the cell under conditions permitting the production of the chimeric protein and recovering the chimeric VEGF-binding protein so produced. The methods described herein provide for the expression and purification of the chimeric VEGF protein in various cell-based expression systems such as protein production in bacterial, mammalian, insect, yeast, and *chymadomonas* cells. Protein expression can be constitutive or inducible with inducers such as copper sulfate, sugars such as galactose, methanol, methylamine, thiamine, tetracycline, or IPTG. After the protein is expressed in the host cells, the host cells are lysed to liberate the expressed protein for purification. Methods of lysing the various host cells are featured in "Sample Preparation-Tools for Protein Research" EMD Bioscience and in the Current Protocols in Protein Sciences (CPPS). The preferred purification method is affinity chromatography such as ion-metal affinity chromatograph using nickel, cobalt, or zinc affinity resins for histidine-tagged chimeric VEGF-binding protein. Methods of purifying histidine-tagged recombinant proteins are described by Clontech using their Talonx cobalt resin and by Novagen in their pET system manual, $10^{th}$ edition. Another preferred purification strategy is by immuno-affinity chromatography, for example, anti-myc antibody conjugated resin can be used to affinity purify myc-tagged chimeric VEGF-binding protein. Enzymatic digestion with serine proteases such as thrombin and enterokinase cleave and release the chimeric VEGF-binding protein from the histidine or myc tag, releasing the chimeric VEGF-binding protein from the affinity resin while the histidine-tags and myc-tags are left attached to the affinity resin.

Besides cell-based expression systems, cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix.

In one embodiment, a continuous cell-free translation system may be used to produce a chimeric VEGF-binding protein. A continuous cell-free translation system capable of producing proteins in high yield is described by Spirin A S. et. al., Science 242:1162 (1988). The method uses a continuous flow design of the feeding buffer which contains amino acids, adenosine triphosphate (ATP), and guanosine triphosphate (GTP) throughout the reaction mixture and a continuous removal of the translated polypeptide product. The system uses *E. coli* lysate to provide the cell-free continuous feeding buffer. This continuous flow system is compatible with both prokaryotic and eukaryotic expression vectors. Large scale cell-free production of the integral membrane protein EmrE multidrug transporter is described by Chang G. el. al., Science 310:1950-3 (2005).

Other commercially available cell-free expression systems include the Expressway™ Cell-Free Expression Systems (Invitrogen) which utilize an *E. coli*-based in-vitro system for efficient, coupled transcription and translation reactions to produce up to milligram quantities of active recombinant protein in a tube reaction format; the Rapid Translation System (RTS) (Roche Applied Science) which also uses an *E. coli*-based in-vitro system; and the TNT Coupled Reticulocyte Lysate Systems (Promega) which uses rabbit reticulocyte-based in-vitro system.

Therapeutic Uses and Formulation

In one embodiment, the invention provides a method of treating an angiogenic disease or disorder, comprising administering to a subject in need thereof a vector comprising a polynucleotide encoding a chimeric VEGF binding polypeptide, wherein the chimeric VEGF-binding polypeptide comprises an Ig-like domain 2 of a vascular endothelial growth factor receptor and an Fc region of immunoglobulin G1 or a reduced immunogenic derivative of an Fc region of immunoglobulin G1. Alternatively, one can administer a pharmaceutical composition comprising a chimeric VEGF binding protein and a pharmaceutically acceptable carrier. In one embodiment, the said subject in need of treatment can be a mammal, such as a dog or a cat, preferably a human.

In another embodiment, the invention provides for a method of treating an angiogenesis-related disease or disorder, comprising administering to a subject in need thereof a pharmaceutical composition comprising a chimeric protein, wherein the chimeric polypeptide comprises an immunoglobulin-like domain 2 of a vascular endothelial growth factor receptor and an Fc region of immunoglobulin G1 or a reduced immunogenic derivative of an Fc region of immunoglobulin G1. In another embodiment, the methods described herein can be used in combination with other treatment options available for angiogenesis-related diseases or disorders.

Angiogenesis, as used herein refers to the sprouting of new blood vessels from pre-existing blood vessels, characterized by endothelial cell proliferation and migration triggered by certain pathological conditions, such as the growth of solid tumors and metastasis.

As used herein, the term "angiogenesis-related disease or disorder" refers to diseases or disorders that are dependent on a rich blood supply and blood vessel proliferation for the disease's pathological progression (eg. metastatic tumors) or diseases or disorders that are the direct result of aberrant blood vessel proliferation (e.g. diabetic retinopathy and hemangiomas). Examples include abnormal vascular proliferation, ascites formation, psoriasis, age-related macular degeneration, thyroid hyperplasia, preclampsia, rheumatoid arthritis and osteo-arthritis, Alzheimer's disease, obesity, pleural effusion, atherosclerosis, endometriosis, diabetic/other retinopathies, ocular neovascularizations such as neovascular glauocoma and corneal neovascularization.

The angiogenesis-related disease or disorder can be selected, for example, from a group consisting of cancer, ascites formation, psoriasis, age-related macular degeneration, thyroid hyperplasia, preclampsia, rheumatoid arthritis and osteoarthritis, Alzheimer's disease, obesity, pleura effusion, atherosclerosis, endometriosis, diabetic/other retinopathies, neovascular glauocoma, age-related macular degeneration, hemangiomas, and corneal neovascularization. In one embodiment, the age-related macular degeneration is wet macular degeneration.

In one embodiment, the anigiogensis-related disease or disorder is cancer, where the rapidly dividing neoplastic cancer cells require an efficient blood supply to sustain their continual growth of the tumor. As used herein, cancer refers to any of various malignant neoplasms characterized by the proliferation of anaplastic cells that tend to invade surrounding tissue and metastasize to new body sites and also refers to the pathological condition characterized by such malignant neoplastic growths. The blood vessels provide conduits to metastasize and spread elsewhere in the body. Upon arrival at the metastatic site, the cancer cells then work on establishing a new blood supply network. Administration of a polynucleotide encoding a chimeric VEGF binding polypeptide or a pharmaceutical composition comprising a chimeric VEGF binding protein and a pharmaceutically acceptable carrier can inhibit angiogenesis. By inhibiting angiogenesis at the primary tumor site and secondary tumor site, embodiments of the invention serve to prevent and limit the progression of the disease.

The effectiveness of a given VEGF-binding chimeric polypeptide as described herein can be evaluated in vitro or in vivo or both, as described, e.g., in the Examples provided herein below. For the avoidance of doubt, one can also use other assays commonly accepted in the field. For example, one can use the "CAM" assay. The chick chorioallantoic membrane (CAM) assay is frequently used to evaluate the effects of angiogenesis regulating factors because it is relatively easy and provides relatively rapid results. A chimeric VEGF-binding polypeptide useful in the methods and compositions described herein will decrease the number of microvessels in the modified CAM assay described by Iruela-Arispe et al., 1999, Circulation 100: 1423-1431(incorporated herein by reference), relative to controls with no chimeric polypeptide added or expressed. The method is based on the vertical growth of new capillary vessels into a collagen gel pellet placed on the CAM. In the assay as described by Iruela-Arispe et al., the collagen gel is supplemented with VEGF (250 ng/gel) in the presence or absence of test proteins/peptides. The extent of the anti-angiogenic effect is measured using FITC-dextran (50 µg/mL) (Sigma) injected into the circulation of the CAM. The degree of fluorescence intensity parallels variations in capillary density; the linearity of this correlation can be observed with a range of capillaries between 5 and 540. Morphometric analyses are performed, for example, by acquisition of images with a CCD camera. Images are then analyzed by importing into an analysis package, e.g., NHImage 1.59, and measurements of fluorescence intensity are obtained as positive pixels. Each data point is compared with its own positive and negative controls present in the same CAM and interpreted as a percentage of inhibition, considering the positive control to be 100% (VEGF alone) and the negative control (vehicle alone) 0%. Statistical evaluation of the data is performed to check whether groups differ significantly from random, e.g., by analysis of contingency with Yates' correction.

Additional angiogenesis assays are known in the art and can be used to evaluate chimeric VEGF-binding polypeptides for use in the methods and compositions described herein. These include, for example, the corneal micropocket assay, hamster cheek pouch assay, the Matrigel assay and modifications thereof, and co-culture assays. Donovan et al. describe a comparison of three different in vitro assays developed to evaluate angiogenesis regulators in a human background (Donovan et al., 2001, Angiogenesis 4: 113-121, incorporated herein by reference). Briefly, the assays examined include: 1) a basic Matrigel assay in which low passage human endothelial cells (Human umbilical vein endothelial cells, HUVEC) are plated in wells coated with Matrigel (Becton Dickinson, Cedex, France) with or without angiogenesis regulator(s); 2) a similar Matrigel assay using "growth factor reduced" or GFR Matrigel; and 3) a co-culture assay in which primary human fibroblasts and HUVEC are co-cultured with or without additional angiogenesis regulator(s)—the fibroblasts produce extracellular matrix and other factors that support HUVEC differentiation and tubule formation. In the Donovan et al. paper the co-culture assay provided microvessel networks that most closely resembled microvessel networks in vivo. However, the basic Matrigel assay and the GFR Matrigel assay can also be used by one of skill in the art to evaluate whether a given chimeric VEGF-binding polypeptide is an angiogenesis inhibitor as necessary for the methods and compositions described herein. Finally, an in vitro angiogenesis assay kit is marketed by Chemicon (Millipore). The Fibrin Gel In Vitro Angiogenesis Assay Kit is Chemicon Catalog No. ECM630. A chimeric VEGF-binding polypeptide as described herein is considered useful in a method or composition for treatment of an angiogenesis-related disease or disorder as described herein if it reduces angiogenesis in any one of these assays by 10% or more relative to a control assay performed without the chimeric VEGF-binding polypeptide. A chimeric VEGF-binding polypeptide as described herein preferably reduces angiogenesis in one or more of these assays by at least 20%, at least 30%, at least 40%, at least 50%, at least 60%, at least 70%, at least 80%, at least 90% or more, up to and including 100% inhibition.

Alternatively, angiogenesis inhibition can be measured functionally downstream, as a reduction or cessation of tumor growth or tumor size. For example, if there is zero growth of tumor mass, or at least 5% reduction in the size of the tumor mass, there is angiogenesis inhibition by a composition or method as described herein.

Any solid tumor that requires an efficient blood supply to keep growing is a candidate target. For example, candidates for the treatment methods described herein include carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma. Abnormal build up and growth of blood vessels in the skin or internal organs in the form of hemangiomas can also be treated according to the methods described herein.

In another embodiment, the invention can be used in preventing blinding blood vessel growth associated with diabetic eye diseases, namely diabetic retinopathy. The methods described herein are designed to antagonize vascular endothelial growth factor (VEGF), a substance naturally produced in the body that promotes blood vessel formation. Released by the retina (light-sensitive tissue in back of the eye) when normal blood vessels are damaged by tiny blood clots due to diabetes, VEGF turns on its receptor, igniting a chain reaction that culminates in new blood vessel growth. However, the backup blood vessels are faulty; they leak, bleed and encourage scar tissue that detaches the retina, resulting in severe loss of vision. Such growth is the hallmark of diabetic retinopathy, the leading cause of blindness among young people in developed countries.

In yet another embodiment, the invention may be used in the treatment of age-related macular degeneration, as it is known that VEGF also contributes to abnormal blood vessel growth from the choroid layer of the eye into the retina, similar to what occurs during the wet or neovascular form of age-related macular degeneration. Macular degeneration, often called AMD or ARMD (age-related macular degeneration), is the leading cause of vision loss and blindness in Americans aged 65 and older. New blood vessels grow (neovascularization) beneath the retina and leak blood and fluid. This leakage causes permanent damage to light-sensitive retinal cells, which die off and create blind spots in central vision or the macula.

In one embodiment, the angiogenesis-related disease or disorder is rheumatoid arthritis. Rheumatoid arthritis (RA) is characterized by synovial tissue swelling, leucocyte ingress and angiogenesis, or new blood vessel growth. The disease is thought to occur as an immunological response to an as yet unidentified antigen. The expansion of the synovial lining of joints in rheumatoid arthritis (RA) and the subsequent invasion by the pannus of underlying cartilage and bone necessitate an increase in the vascular supply to the synovium, to cope with the increased requirement for oxygen and nutrients. Angiogenesis is now recognised as a key event in the formation and maintenance of the pannus in RA (Paleolog, E. M., 2002, Arthritis Res. 4(Suppl 3):S81-S90). Even in early RA, some of the earliest histological observations are blood vessels. A mononuclear infiltrate characterizes the synovial tissue along with a luxuriant vasculature. Angiogenesis is integral to formation of the inflammatory pannus and without angiogenesis, leukocyte ingress could not occur (Koch, A. E., 2000, Ann. Rheum. Dis.; 59(Suppl 1):i65-i71). Disruption of the formation of new blood vessels would not only prevent delivery of nutrients to the inflammatory site, it could also reduce joint swelling due to the additional activity of VEGF, a potent pro-angiogenic factor in RA, as a vascular permeability factor.

In one embodiment, the angiogenesis-related disease or disorder is Alzheimer's disease. Alzheimer's disease (AD) is the most common cause of dementia worldwide. AD is characterized by an excessive cerebral amyloid deposition leading to degeneration of neurons and eventually to dementia. The exact cause of AD is still unknown. It has been shown by epidemiological studies that long-term use of non-steroidal anti-inflammatory drugs, statins, histamine H2-receptor blockers, or calcium-channel blockers, all of which are cardiovascular drugs with an anti-angiogenic effects, seem to prevent Alzheimer's disease and/or influence the outcome of AD patients. Therefore, it has been speculated that in AD angiogenesis in the brain vasculature may play an important role in AD. In Alzheimer's disease, the brain endothelium secretes the precursor substrate for the beta-amyloid plaque and a neurotoxic peptide that selectively kills cortical neurons. Moreover amyloid deposition in the vasculature leads to endothelial cell apoptosis and endothelial cell activation which leads to neovascularization. Vessel formation could be blocked by the VEGF antagonist SU 4312 as well as by statins, indicating that anti-angiogenesis strategies based on VEGF inhibition can interfere with endothelial cell activation in AD (Schultheiss C., el. al., 2006, Angiogenesis. 9(2):59-65; Grammas P., et. al., 1999, Am. J. Path., 154(2):337-42) and can be used for preventing and/or treating AD.

In one embodiment, the angiogenesis-related disease or disorder is obesity. It has been shown that the angiogenesis inhibitor, TNP-470 was able to prevent diet-induced and genetic obesity in mice (Ebba Bråkenhielm et. al., Circulation Research, 2004; 94:1579). TNP-470 reduced vascularity in the adipose tissue, thereby inhibiting the rate of growth of the adipose tissue and obesity development. Thus, inhibition of angiogenesis can be therapeutic for obesity.

In one embodiment, the angiogenesis-related disease or disorder is endometriosis. Excessive endometrial angiogenesis is proposed as an important mechanism in the pathogenesis of endometriosis (Healy, D L., et. al., 1998, Human Reproduction Update, 4:736-740). The endometrium of patients with endometriosis shows enhanced endothelial cell proliferation. Moreover there is an elevated expression of the cell adhesion molecule integrin vß3 in more blood vessels in the endometrium of women with endometriosis when compared with normal women. Strategies that inhibit angiogenesis can be used to treat endometriosis.

In one embodiment, the invention provides for a pharmaceutical composition comprising a chimeric VEGF-binding protein and a pharmaceutically acceptable carrier. In another embodiment, the invention provides for a pharmaceutical composition comprising an expression vector carrying a chimeric DNA sequence that encodes the chimeric VEGF-binding protein and a pharmaceutically acceptable carrier. In yet another embodiment, the invention provides for a pharmaceutical composition comprising the host viral cells (vectors) harboring the chimeric DNA sequence that encodes the chimeric VEGF-binding protein and a pharmaceutically acceptable carrier.

As used herein, the term "pharmaceutical composition" refers to the active agent in combination with a pharmaceutically acceptable carrier of chemicals and compounds commonly used in the pharmaceutical industry. The term "pharmaceutically acceptable carries" excludes tissue culture medium.

For angiogenic diseases or disorders that are accessible externally on the skin, such as dermal hemangiomas and skin cancer lesions (melanoma), gene therapy virus, expression vectors, or chimeric VEGF-binding protein can be preferably applied topically to the hemangioma or cancer lesion site in a therapeutically effective amount in admixture with pharmaceutical carriers, in the form of topical pharmaceutical compositions. The gene therapy virus can be in the form of an adenovirus, adeno-associated virus or lentivirus. Such compositions include solutions, suspensions, lotions, gels, creams, ointments, emulsions, skin patches, etc. All of these dosage forms, along with methods for their preparation, are well known in the pharmaceutical and cosmetic art. HARRY'S COSMETICOLOGY (Chemical Publishing, 7th ed. 1982); REMINGTON'S PHARMACEUTICAL SCIENCES (Mack Publishing Co., 18th ed. 1990). Typically, such topical formulations contain the active ingredient in a concentration range of 0.1 to 100 mg/ml, in admixture with suitable vehicles. A suitable vehicle will not promote an immune response to the chimeric polypeptides described herein. For gene therapy viruses, the dosage ranges from $10^{(6)}$ to $10^{(14)}$ particles per application. Other desirable ingredients for use in such preparations include preservatives, co-solvents, viscosity building agents, carriers, etc. The carrier itself or a component dissolved in the carrier may have palliative or therapeutic properties of its own, including moisturizing, cleansing, or anti-inflammatory/anti-itching properties. Penetration enhancers may, for example, be surface active agents; certain organic solvents, such as di-methylsulfoxide and other sulfoxides, dimethyl-acetamide and pyrrolidone; certain amides of heterocyclic amines, glycols (e.g. propylene glycol); propylene carbonate; oleic acid; alkyl amines and derivatives; various cationic, anionic, nonionic, and amphoteric surface active agents; and the like.

Topical administration of a pharmacologically effective amount may utilize transdermal delivery systems well known in the art. An example is a dermal patch. Alternatively the biolistic gene gun method of delivery may be used. The gene gun is a device for injecting cells with genetic information, originally designed for plant transformation. The payload is an elemental particle of a heavy metal coated with plasmid DNA. This technique is often simply referred to as biolistics. Another instrument that uses biolistics technology is the PDS-1000/He particle delivery system. The chimeric VEGF-binding protein, expression vector, and/or gene therapy virus can be coated on minute gold particles, and these coated particles are "shot" into biological tissues such as hemangiomas and melanoma under high pressure. An example of the gene gun-based method is described for DNA based vaccination of cattle by Loehr B. I. et. al. J. Virol. 2000, 74:6077-86.

In one embodiment, the compositions described herein can be administered directly by injection. If the solid tumors and hemangiomas are accessible by injection, the chimeric VEGF-binding protein, expression vector, and/or viral vector can be administered by injection directly to the tumor mass as a pharmaceutical formulation. The preferred formulation is also sterile saline or Lactated Ringer's solution. Lactated Ringer's solution is a solution that is isotonic with blood and intended for intravenous administration.

In the treatment and prevention of diabetic retinopathy and wet macular degeneration, the present invention, which is much smaller then other VEGF-binding protein in market and in clinical trials, can be applied to the eye by injection as a pharmaceutical formulation. The injection directly introduces the chimeric VEGF-binding protein into the vitreous humor. In one embodiment, the invention compositions can be formulated as an eye drop solution for direct application on the eyes.

In addition to topical therapy, the compositions described herein can also be administered systemically in a pharmaceutical formulation. Systemic routes include but are limited to oral, parenteral, nasal inhalation, intratracheal, intrathecal, intracranial, and intrarectal. The pharmaceutical formulation is preferably a sterile saline or lactated Ringer's solution. For therapeutic applications, the preparations described herein are administered to a mammal, preferably a human, in a pharmaceutically acceptable dosage form, including those that may be administered to a human intervenously as a bolus or by continuous infusion over a period of time, by intramuscular, intraperitoneal, intracerebrospinal, subcutaneous, intra-arterial, intrasynovial, intrathecal, oral, topical, or inhalation routes. A preferred embodiment is the intramuscular injection of AAV viral vectors encoding a chimeric VEGF protein and/or its variant forms. The compositions described herein are also suitably administered by intratumoral, peritumoral, intralesional or perilesional routes, to exert local as well as systemic effects. The intraperitoneal route is expected to be particularly useful, for example, in the treatment of ovarian tumors. For these uses, additional conventional pharmaceutical preparations such as tablets, granules, powders, capsules, and sprays may be preferentially required. In such formulations further conventional additives such as binding-agents, wetting agents, propellants, lubricants, and stabilizers may also be required. In one embodiment, the therapeutic compositions described herein are formulated in a cationic liposome formulation such as those described for intratracheal gene therapy treatment of early lung cancer (Zou Y. et. al., Cancer Gene Ther. 2000 May; 7(5):683-96). The liposome formulations are especially suitable for aerosol use in lung cancer patients. Vector DNA and/or virus can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et. al. Gene Ther. 1999, 6:1438-47). Other techniques in formulating expression vectors and virus as therapeutics are found in "DNA-Pharmaceuticals: Formulation and Delivery in Gene Therapy, DNA Vaccination and Immunotherapy" by Martin Schleef (Editor) December 2005, Wiley Publisher, and "Plasmids for Therapy and Vaccination" by Martin Schleef (Editor) May 2001, are incorporated herein as reference. In one embodiment, the dosage for viral vectors is $10^{(6)}$ to $1\times10^{(14)}$ viral vector particles per application per patient.

The route of administration, dosage form, and the effective amount vary according to the potency of the chimeric VEGF receptor proteins, expression vectors and viral vectors, their physicochemical characteristics, and according to the treatment location. The selection of proper dosage is well within the skill of an ordinarily skilled physician. Topical formulations can be administered up to four-times a day.

In one embodiment, dosage forms include pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of chimeric protein include polysaccharides such as sodium carboxymethylcellulose or methylcellulose, polyvinylpyrrolidone, polyacrylates, polyoxyethylene-polyoxypropylene-block polymers, polyethylene glycol and wood wax alcohols. For all administrations, conventional depot forms are suitably used. Such forms include, for example, microcapsules, nano-capsules, liposomes, plasters, inhalation forms, nose sprays, sublingual tablets, and sustained release preparations. For examples of sustained release compositions, see U.S. Pat. No. 3,773,919, EP 58,481A, U.S. Pat. No. 3,887,699, EP 158,277A, Canadian Patent No. 1176565, U. Sidman et al., Biopolymers 22:547 (1983) and R. Langer et al., Chem. Tech. 12:98 (1982). The chimeric protein will usually be formulated in such vehicles at a concentration of about 0.1 mg/ml to 100 mg/ml and the viral vector should be in the range of $10^{(6)}$ to $1\times10^{(14)}$ viral vector particles per application per patient.

In one embodiment, other ingredients may be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, the pharmaceutical formulation to be used for therapeutic administration must be sterile. Sterility is readily accomplished by filtration through sterile filtration membranes (e.g., 0.2 micron membranes). The chimeric VEGF receptor protein ordinarily will be stored in lyophilized form or as an aqueous solution if it is highly stable to thermal and oxidative denaturation. The pH of the chimeric VEGF receptor protein preparations typically will be about from 6 to 8, although higher or lower pH values may also be appropriate in certain instances.

For the prevention or treatment of angiogenic disease or disorder, the appropriate dosage of chimeric VEGF receptor protein and/or viral vectors will depend upon the type of disease or disorder to be treated, the severity and course of the disease, whether the chimeric VEGF receptor proteins are administered for preventative or therapeutic purposes, previous therapy, the patient's clinical history and response to the chimeric VEGF receptor protein and/or viral vectors and the discretion of the attending physician. The chimeric VEGF receptor protein and/or viral vectors are suitably administered to the patient at one time or over a series of treatments. For purposes herein, the "therapeutically effective amount" of a chimeric VEGF receptor protein or viral vector is an amount that is effective to either prevent, lessen the worsening of, alleviate, or cure the treated condition, in particular that amount which is sufficient to reduce or inhibit the proliferation of vascular endothelium in vivo.

This invention is further illustrated by the following example which should not be construed as limiting. The contents of all references cited throughout this application, as well as the figures and tables are incorporated herein by reference.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLE

VEGF binding proteins, in the form of mAb's, soluble VEGF receptor extracellular domains, or heterologous constructs derived from subdomains of VEGF receptors (referred to as VEGF-Traps) have been shown to exhibit potent anti-tumor effects in preclinical (1, 2) and clinical studies (3). Studies to date have largely utilized direct systemic protein delivery of these proteins. Because of the requirement for sustained delivery of anti-angiogenic agents to maintain an anti-tumor effect, there is interest in investigating the use of gene therapy based approaches for delivering VEGF binding proteins in order to achieve sustained systemic delivery of protein. In a prior report, (2) it was noted that systemically delivered adenoviruses could secrete a high level of soluble VEGF receptor extracellular domains and control the growth of several different human tumor xenografts in vivo. This adenovirus based system is less favorable for clinical use secondary to issues of immune mediated reduction in transgene expression and potential for organ specific (e.g. liver) toxicity after systemic virus delivery. Because of these limitations the strategy of delivering these proteins using more clinically acceptable vectors delivered via intramuscular injection was explored.

To this end, a smaller, neutrally charged VEGF binding protein VEGF-trap 3 (VT3) was designed and expressed, more appropriate for the smaller packaging capability of adeno-associated virus, as well as those with enhanced charge properties compared to the original VEGF-Trap described by Holash et al. (1) This modification entailed removing one of two basic Ig VEGF binding domain in the parental VEGF-Trap 1 (VT1) proteins. It was found that this modified trap retained a similar binding affinity to VEGF compared to VT1. The modified VEGF-Trap3 (VT3) yielded significantly higher levels of serum protein when delivered via an AAV vector using a direct intramuscular delivery technique. The unique features of this Trap make it particularly suitable for gene therapy approaches for anti-VEGF anti-angiogenic therapeutic strategies.

Materials and Methods.

VEGF Binding Proteins

Purified VEGF-Trap 1 (VT1) was obtained as a gift from Regeneron Pharmaceuticals. Recombinant human Flt-1/Fc chimera (R&D System 321-FL), recombinant human KDR/Fc chimera (R&D System 357-KD) and recombinant human IgG$_1$ Fc (R&D System 110-HG) were purchased from R&D Systems.

Engineering VEGF-Trap1 and VEGF-Trap3 Encoding AAV Vectors

In order to construct an AAV vector encoding VEGF-Trap 1 (VT1), fusion PCR of transgene encoding oligos was used to create a full length VEGF-Trap construct encoding the signal sequence of VEGF-receptor 1 (Amino acids 1-26 of Genbank Accession No.: BC039007, SEQ. ID. No.: 1) fused directly to the second Ig domain (Amino acids 129-231 of Genbank Accession No.: BC039007, SEQ. ID. No.: 1) fused directly to the third Ig domain of VEGF-Receptor 2 (amino acids 226-327 of Genbank Accession No.: AF035121, SEQ. ID. No.: 9) fused directly to the huIgG1 (amino acids 247-473 of Genbank Accession No.: BC092518) as described Holash et al. (Holash et al., 2002).

Vegf-Trap 3 (VT3) was similarly constructed by attaching the second Ig domain of Flt-1 to Fc-huIgG$_1$. The final construct encodes the signal sequence of VEGF-receptor 1 (Amino acids 1-26 of Genbank Accession No.: BC039007, SEQ. ID. No.: 1) the second Ig domain (Amino acids 129-231 of Genbank Accession No.: BC039007, SEQ. ID. No.: 1) fused directly to the huIgG1 (amino acids 247-473 of Genbank Accession No.: BC092518). Final constructs encoding both VT1 and VT3 were sequenced in both sense and anti-sense strands to confirm correct sequence and orientation.

Production of recombinant AAV vectors encoding VEGF-Trap1 and VEGF-Trap 3 was performed by triple transfection as described previously (4). Briefly, the pAAV-VEGF-Trap vector plasmids were co-transfected with AAV helper plasmid pLT-RC02 (Jeng-Shin Lee and Richard Mulligan, unpublished) and adenovirus helper miniplasmid pHGTI-Adeno1 (John Gray and Richard Mulligan, unpublished) into 293 cells. 48 hours after transfection, the cells were harvested and lysed. After Bezonase treatment and removal of cell debris by low speed centrifugation, the recombinant AAV particles were purified by iodixanol density gradient. The 40% iodixanol fraction containing rAAV particles was recovered, dialyzed extensively against PBS and titered by dot-blot hybridization using the CMV promoter as the probe.

pLT-RC02 encodes hybrid Rep proteins from AAV serotypes 1 and 2, and Cap proteins from serotype 1. When used in the triple tranfection production system, pLT-RC02 plasmid packages AAV particles at a comparable level relative to that obtained with AAV serotype 2 Rep/Cap expression plasmid. But the resultant vector particles transduced skeletal muscles at significantly higher efficiency than regular serotype 2 vectors (Jeng-Shin Lee and Richard Mulligan, unpublished) as reported previously for AAV serotype 1 vectors.

Protein Purification of VEGF-Trap 3.

Stable production of VEGF-Trap 1 and VEGF-Trap 3 in 293T cell was achieved by infection with lentiviruses encoding the respective VEGF-Trap proteins. Stable production of the VEGF-Traps was confirmed by ELISA. Serum free Dulbecco's Modified Eagle Medium (Gibco 11965-092) conditioned media from infected cells was subsequently pooled and subjected to Protein A affinity chromatography.

NProtein A Sepharose 4 Fast Flow (Amersham Biosciences 17-5280-04) columns were prepared according to manufacturer's instructions. In order to ensure proper ionic strength, serum free conditioned media was supplemented with 3.3M NaCl prior to being applied to the column. Samples were loaded overnight at 4° C. then column was washed with 5 bed volumes of 50 mM Tris, 150 mM NaCl and 0.1% Tween-20 pH 8.0. VEGF-Trap proteins were eluted with 1-3 bed volumes 0.1M Citrate pH3 and neutralized with 2M Tris pH8.5. Elutes were dialyzed against phosphate-buffered saline (PBS) (Gibco) in 10,000 MWCO dialysis cassettes (Pierce 66380) at 4° C., overnight. Finally the samples were concentrated by Amicon Ultra low binding centrifugal filter devices (Millipore UFC901008) and purity was assessed by SDS PAGE and Coomassie staining.

Protein Characterization—Glycosylation and Western Blot Analysis

Purified protein samples were subjected to SDS PAGE (12% gel, Life Gels, NH21-012) at 100V for 45 minutes then the gel was transferred in a wet electrotransfer system at a constant current of 35 mA for 2 hours. Following the transfer, supported nitrocellulose membrane (Bio-Rad 162-0095) was blocked with 10% Non-Fat Dried Milk in PBS-0.1% Tween-20 at room temperature for 1 hour. Membrane was probed with anti-Flt-1 (R&D System AF321or Imclone) primary and HRP conjugated anti-goat-IgG secondary antibody or with HRP-conjugated primary antibody against human-IgG-Fc (Sigma A0170) diluted in PBS-0.1% Tween-20. Blots were developed by using ECL-Plus (Amersham Biosciences RPN2132) HRP substrate and Kodak Biomax Chemiluminescence Film (Kodak 178 8207).

In order to remove all N and O-linked carbohydrates, protein samples were denatured at 100° C. for 5 minutes then incubated with PNGase F, α-2(3,6,8,9)Neuraminidase, O-Glycosidase, β(1-4)-Galactosidase and β-N-Acetylglucosaminidase enzymes (Sigma, E-DEGLY) overnight at 37° C. Extend of the glycosylation was assessed by SDS-PAGE of deglycosylated and non-deglycosylated protein samples. Following the electrophoresis the gel was Coomassie stained (Gradipore, Gradiflash SG-010) for 5 h at room temperature then distained with 6% Acetic Acid at room temperature for 20 hours.

Binding Affinity Measurement

Binding affinities of Vegf-Trap 3, recombinant VEGF-Trap 1 (gift of Regeneron pharmaceuticals), recombinant human Flt-1/Fc chimera (R&D System 321-FL), recombinant human KDR/Fc chimera (R&D System 357-KD) and recombinant human $IgG_1$ Fc (R&D System 110-HG) were measured by ELISA (R&D System DVE00) as previously described by Holash et al. (1.)

Serum VEGF-Trap Detection—VEGF-Trap ELISA

Immulon-4 HBX plates are coated with 25 ng/well human Vegf165 (R&D System 293 VE) overnight at 4° C. Plates are blocked with 3% Non-Fat Dried Milk in PBS-0.1% Tween-20 at room temperature for 1 hour.

Standards and serum samples are diluted in PBS-10% mouse serum-0.1% Tween-20 solution, applied to the plate and incubated at room temperature for 1 hour. Plates are washed with PBS-0.1% Tween-20 five times. Diluted (1:5000), HRP-conjugated detection antibody against human-IgG-Fc (Sigma A0170) is added to the wells. After 1 hour incubation at room temperature plates are washed with PBS-0.1% Tween-20. O.D. is read at 405 nm within 10 min of adding HRP-substrate (KPL 50-66-06).

Pharmacokinetic Analysis—BALB/c Injection with Protein

BALB/c and C57Bl/6 mice (20-25 g) were injected with 100 ug/animal Vegf-Trap 3 or VEGF-Trap 1 s.c. The mice were bled at 1, 6, 24, 48, 72, 96, 120, 144 hours after injection. The levels of Vegf-Trap3 and VEGF-Trap 1 were measured by ELISA.

AAV-Delivery

Mice were obtained from Jackson Labs (Bar Harbor, Me.) and maintained in a pathogen-free animal facility at Harvard Institute of Medicine, Boston, Mass. Animal studies were approved by the Standing Committee on Animals of Harvard Medical School.

Tumor Growth Studies

Animal studies were carried out in the animal facility at Childrens Hospital, Boston, Mass., in accordance with federal, local and institutional guidelines. Immunocompetent, male C57Bl6/J mice (Jackson Labs, Bar Harbor, Me.) 7-9 weeks of age were used. Lewis Lung Carcinoma (LLC) cells (American Type Culture Collection, Rockville, Md.) were grown and maintained as described earlier (5) A suspension of $5 \times 10^6$ tumor cells in 0.1 ml DMEM was injected s.c. into the dorsa of mice at the proximal midline.

Mice were weighed and tumors were measured every 3 to 5 days in two diameters with a dial caliper. Volumes were determined using $a^2 \times b \times 0.52$ formula, where a is the shortest and b is the longest diameter. When the average tumor volume reached approximately 100 $mm^3$ mice were randomized into seven treatment groups (n=4). VEGF-Trap proteins and the placebo control were administered twice a week subcutaneously. Upon completion of the experiment mice were euthanized by $CO_2$ asphyxiation. Tumors were fixed in 10% buffered formalin (Fisher Scientific) overnight at 4° C. then processed for immunohistochemistry as described previously.(6)

Results

Two different expression cassettes were ligated into AAV vectors to create AAV-VT 1 encoding VEGF-Trap 1 (Holash et al, 2002) and AAV-VEGF-Trap 3 as shown in FIG. 1.

Figure 2:
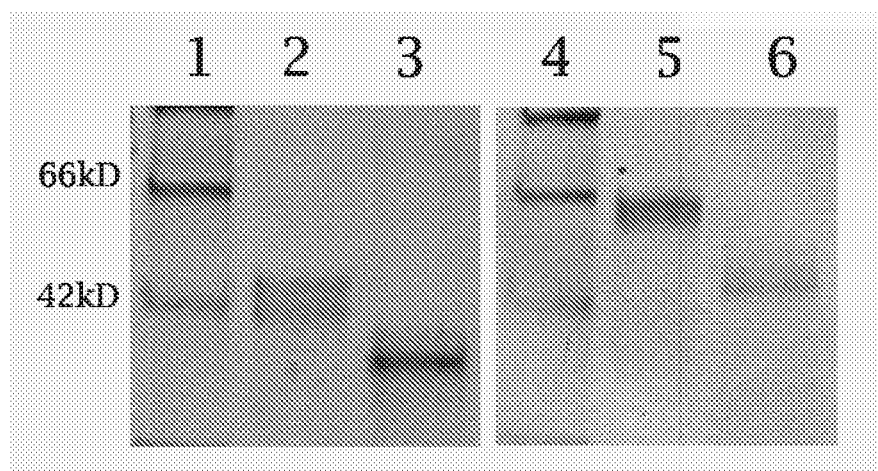
FIG. 2. Deglycosylation of VEGF-Trap 1 and VEGF-Trap 3 using PNGase F, α-2(3,6,8,9)Neuraminidase and O-Glycosidase enzymes. SDS-PAGE (12% gel) followed by Coomassie staining. Lane 1 and 4 CandyCane Glycoprotein Molecular weight Marker (Molecular Probes). Lane 2 VEGF-Trap 3. Lane 3 VEGF-Trap 3 after deglycosylation. Lane 5 VEGF-Trap 1. Lane 6 VEGF-Trap 1 after deglycosylation.
Figure 3:
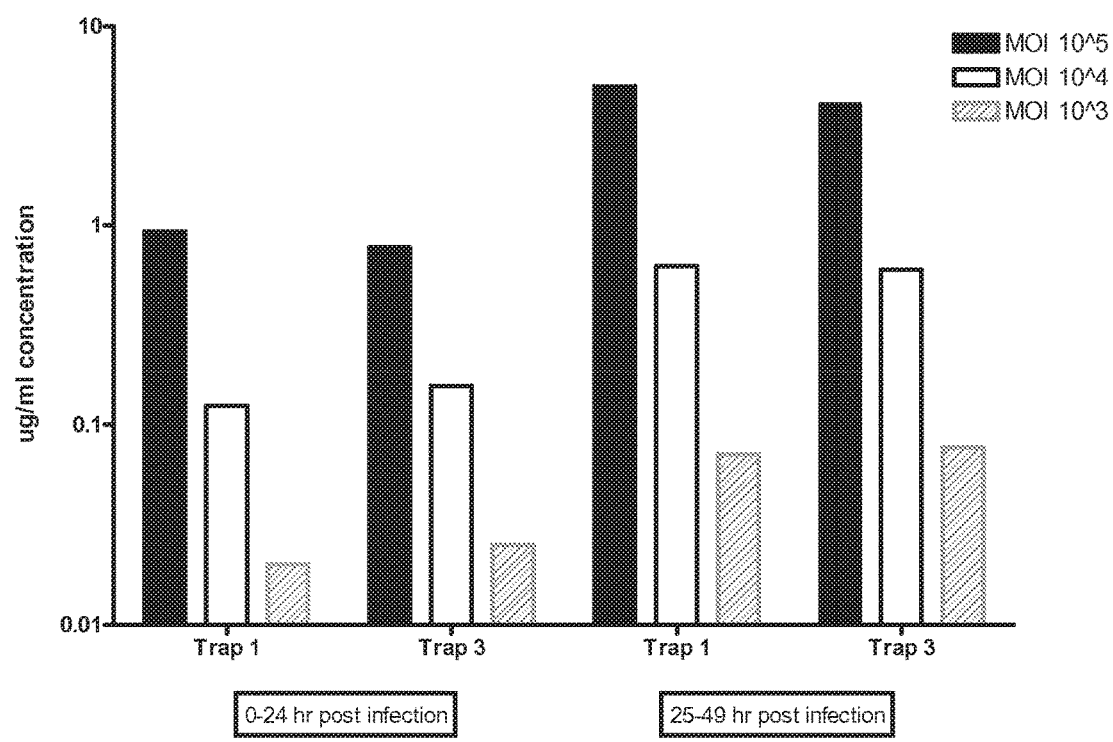
FIG. 3. Concentrations of VEGF-Trap 1 or VEGF-Trap 3 following infection of 1.7E6 293T cells in culture. Cells were exposed to AAV encoding either VEGF-Trap 1 or VEGF-Trap 3 at the indicated multiplicity of infection.

293T cells stably expressing these construct yielded purified proteins from 293 cell conditioned media of the predicted (VT1-48.7 kDa, VT3-37.4 kDa) size when analyzed under deglycosylating conditions (FIG. 2-lane 3-VT3, 6-VT1). Furthermore, similar levels of protein were produced when 293T cells were infected with AAV virus as assessed by Elisa. As shown in FIG. 3, there was a similar dose dependent rise in concentration of both VEGF-Trap 1 and VEGF-Trap 3 with increasing multiplicity of infection. The measured mean concentrations of these two proteins were within 200% of each other and this was not different statistically.

Figure 4:
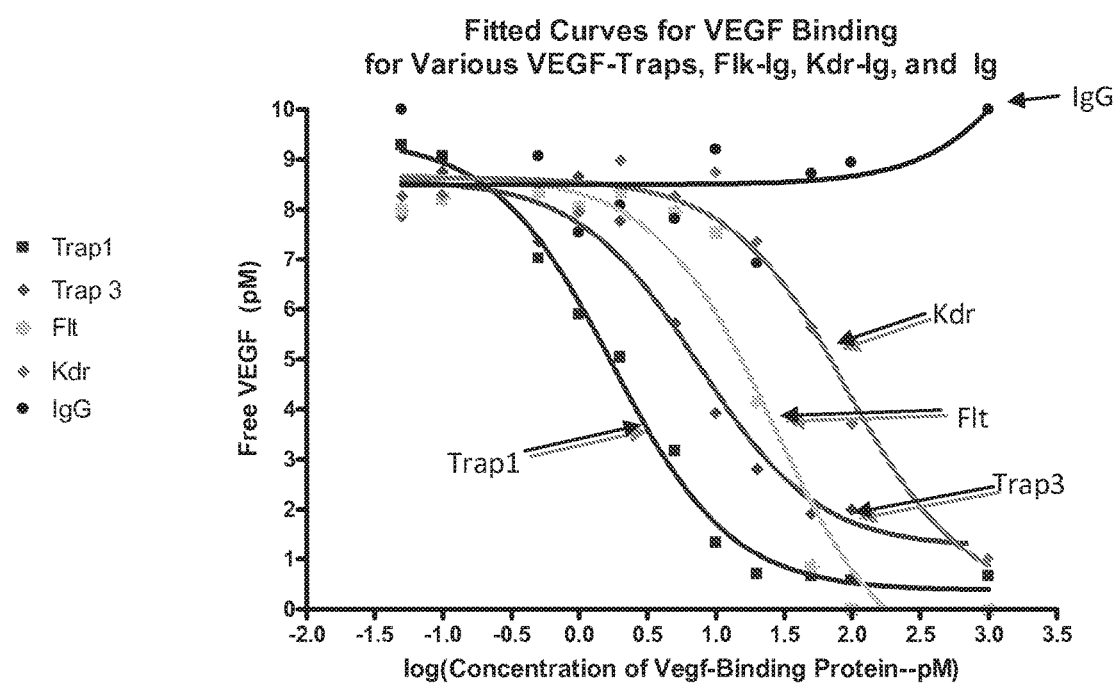
FIG. 4. Binding affinity analysis of VEGF-binding proteins. In brief, a fixed concentration of human VEGF$_{165}$ (10 pM) was incubated overnight at room temperature with varying concentrations (0.05 pM to 1000 pM) of VEGF binding proteins. 20 hours later, concentration of unbound VEGF$_{165}$ was measured by ELISA. Binding curves were fitted using Prizm software.

A binding affinity analysis (FIG. 4) revealed that both VT1 and VT3 had a superior binding affinity for VEGF compared to the full-length VEGF-Receptor 1 and Receptor 2 extracellular domains. VT1 binding affinity was estimated at 1.8 pM and that of VT3 at 7.3 pM. VEGF-R1 extracellular domain Ig fusion demonstrated a binding affinity of 25.9 pM and VEGF-R2 extracellular domain, 92.3 pM.

Figure 5:
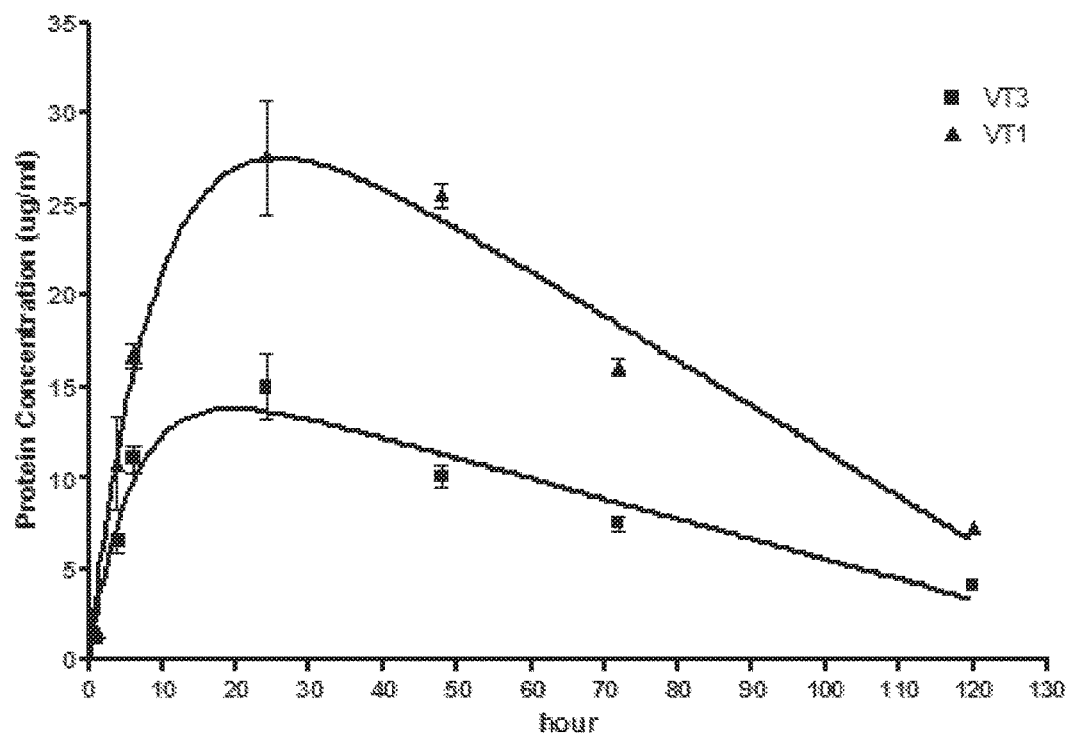
FIG. 5. In Vivo pharmacokinetic analysis after subcutaneous injection of 100 μg of either VEGF-Trap-1 or VEGF-Trap-3 into Balb/C mice. Mice were bled at 1, 4, 6, 24, 48, 72, 120 hours after injection. Levels of various VEGF binding proteins were measured by ELISA using purified VEGF-Trap proteins as standard.
Figure 6:
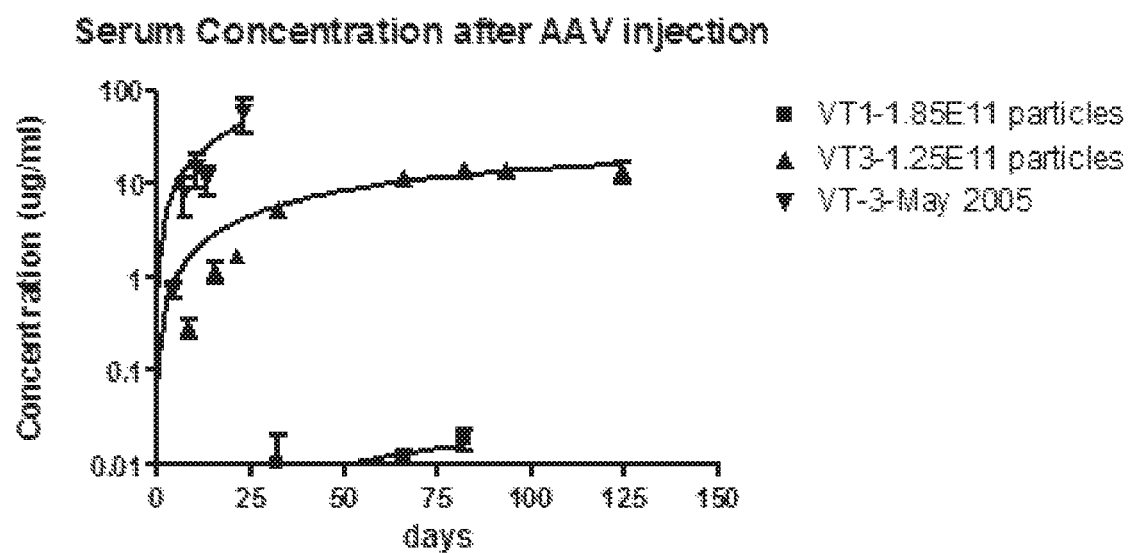
FIG. 6. Plasma concentration of VEGF binding proteins after AAV injection. Nu/Nu mice were intramuscularly injected with recombinant AAV vectors encoding for either VT1 or VT3. Mice were bled on 4, 7, 8, 10 13, 15, 21, 23, 32, 66, 82, 93, 124 days after injection. Plasma concentration of VT1 and VT3 was measured by ELISA using human VEGF$_{165}$ to bind VEGF-Trap and antibody against human IgG$_1$-Fc to detect the captured proteins.

Following subcutaneous deposition of 100 µg of purified protein into the flanks of nude mice, a slightly higher peak serum concentration of VEGF-Trap 1 was achieved (FIG. 5) (27.5 µg/ml versus 14 µg/ml) although both proteins were still present in the serum at 120 hours post injection. This finding was in marked contrast to the levels of protein detected after AAV based gene delivery into skeletal muscle in which we noted that VEGF-Trap 3 had a markedly improved pharmacokinetic profile compared to VEGF-Trap 1. For this experiment, mice were injected intramuscularly with 1.25 (VT3)-1.85 (VT1) E11 AAV particles in a total volume of 50 µl. Serial serum ELISA measurements revealed that while AAV VT3 protein could be detected at approximately 10 µg/ml for >120 days. AAV VT1 protein was present in the serum at <0.1 µg/ml for the duration (120 days) of analysis (FIG. 6). These data showed that AAV-mediated delivery of VT3 protein result in a sustained and longer term expression of VT3 in vivo, and that is significantly more effective than the AAV mediated delivery of VT1.

Figure 7:
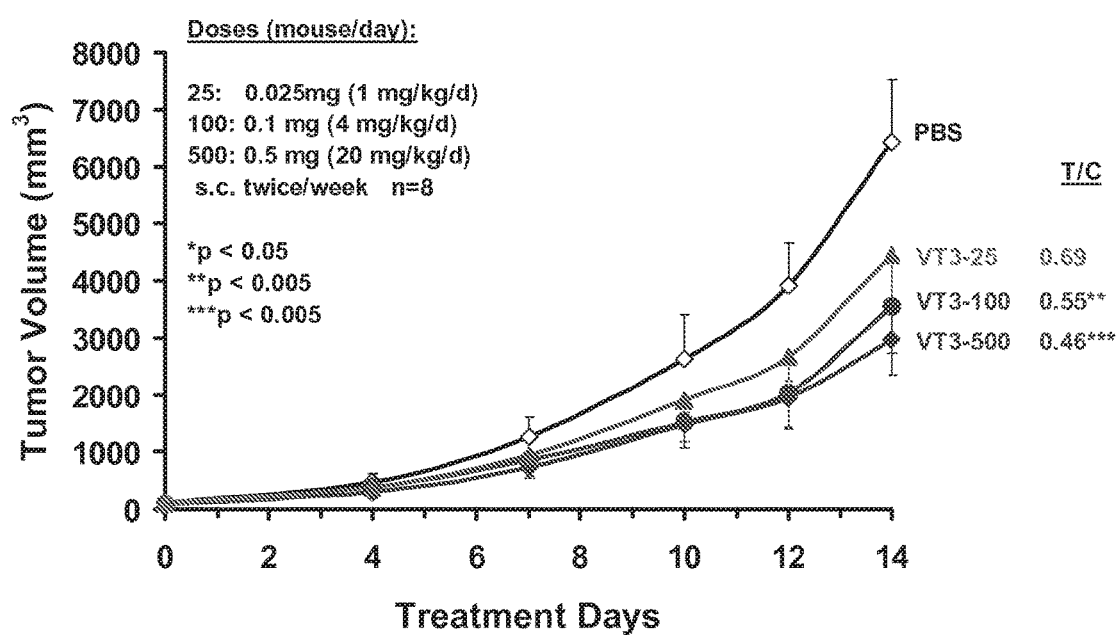
FIG. 7. Treatment of LLC with VEGF-Trap3 protein. LLC cells were implanted subcutaneously in the dorsa of C57Bl/J6 mice (n=8). Mice were treated systemically with 0.025 mg, 0.1 mg or 0.5 mg of VT3 s.c. injections twice week. Control mice were treated with PBS. Tumor volume was measured every 2 to 4 days. T/C is indicated. VT1 was not detectable up to day 23.
Figure 8:
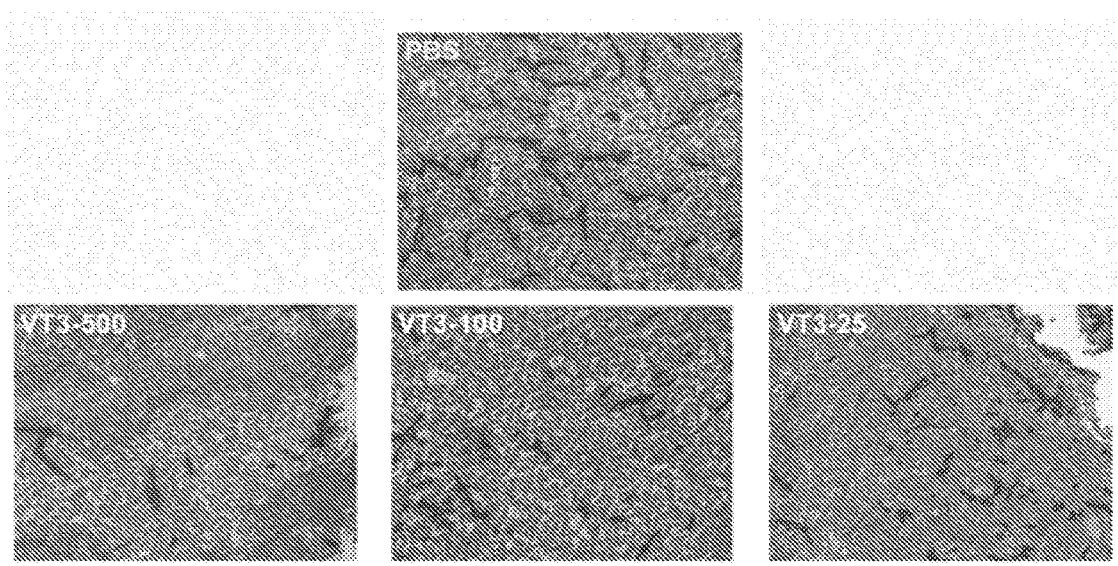
FIG. 8. CD31 staining of LLC tumors treated with three different levels of VEGF-Trap 3 dosing compared to PBS treated controls. A dose dependent reduction in the number of vessels is observed with increasing VEGF-Trap 3 levels.

The level of VEGF-Trap 3 required to inhibit tumor growth was determined. This was performed using the angiogenesis sensitive subcutaneous Lewis lung carcinoma tumor model. Animals were injected in the flank with 5E5 cells. 7 days later biweekly treatment with VEGF-Trap 3 was performed. As observed in FIG. 7, there was a dose dependent inhibition of LLC tumor growth, while animals receiving as low 1 mg/kg/dose showed growth inhibition compared to PBS treated mice, the best growth inhibition was observed with biweekly dosing of 4 mg/kg. Serum VEGF-Trap 3 levels were also measured at two points during the study. At Day 6, 72 hours after the second treatment dose, the average VEGF-Trap 3 levels were 3.6, 10.1, and 62 µg/ml for the 1, 2, and 4 mg/kg dosing regimens respectively. At day 14, 96 hours after the $4^{th}$ dose, VEGF-Trap levels were 0.7, 5.9, and 30.2 µg/ml for the 1, 2, and 4 mg/kg dosing regimens respectively.

Gene based delivery of anti-angiogenic proteins offers theoretical advantages over repeated protein administrations of such proteins. A continuous and persistent level of angiogenesis inhibition is required to optimize the efficacy of this therapy. Of the various modalities of gene delivery currently available, AAV based transduction of skeletal muscle is considered a relatively safe modality and clinical trials using this modality are underway(4). However, after gene delivery, a variety of factors may influence the pharmacokinetic profile of the delivered protein. The original VEGF-Trap protein was designed to remove positively charged motifs compared to full length VEGF receptor extracellular domains and thereby reduce interactions with negatively charged proteoglycans in the extracellular matrix following subcutaneous deposition. In the initial efforts to develop gene therapy vectors capable of delivering a sufficiently high serum level of anti-angiogenic activity by using the VEGF-Trap 1, it was found (FIG. 6) that levels of VEGF-Trap 1 secreted by AAV vectors after IM injection were very low. The VEGF-trap 1 was modified by removing the $3^{rd}$ Ig domain of the VEGF-Receptor 2, one of two VEGF binding motifs present in VEGF-Trap 1. This modification further reduced the size and charge of the protein. Following AAV based transduction of skeletal muscle, the levels of VEGF-Trap 3 achieved were 2 logs greater than those could be achieved from a VEGF-Trap 1 expressing vector.

The references cited herein and throughout the specification are incorporated herein by reference.

REFERENCES

1. Holash, J., Davis, S., Papadopoulos, N., Croll, S. D., Ho, L., Russell, M., Boland, P., Leidich, R., Hylton, D., Burova, E., Ioffe, E., Huang, T., Radziejewski, C., Bailey, K., Fandl, J. P., Daly, T., Wiegand, S. J., Yancopoulos, G. D., and Rudge, J. S. VEGF-Trap: a VEGF blocker with potent antitumor effects. Proceedings of the National Academy of Sciences of the United States of America, 99: 11393-11398, 2002.
2. Kuo, C. J., Farnebo, F., Yu, E. Y., Christofferson, R., Swearingen, R. A., Carter, R., von Recum, H. A., Yuan, J., Kamihara, J., Flynn, E., D'Amato, R., Folkman, J., and Mulligan, R. C. Comparative evaluation of the antitumor activity of antiangiogenic proteins delivered by gene transfer. Proceedings of the National Academy of Sciences of the United States of America, 98: 4605-4610, 2001.
3. Hurwitz, H., Fehrenbacher, L., Novotny, W., Cartwright, T., Hainsworth, J., Heim, W., Berlin, J., Baron, A., Griffing, S., Holmgren, E., Ferrara, N., Fyfe, G., Rogers, B., Ross, R., and Kabbinavar, F. Bevacizumab plus irinotecan, fluorouracil, and leucovorin for metastatic colorectal cancer. New England Journal of Medicine, 350: 2335-2342, 2004.
4. Flotte, T. R., Brantly, M. L., Spencer, L. T., Byrne, B. J., Spencer, C. T., Baker, D. J., and Humphries, M. Phase I trial of intramuscular injection of a recombinant adeno-associated virus alpha 1-antitrypsin (rAAV2-CB-hAAT) gene vector to AAT-deficient adults. Human Gene Therapy, 15: 93-128, 2004.
5. Kisker, O., Becker, C. M., Prox, D., Fannon, M., D'Amato, R., Flynn, E., Fogler, W. E., Sim, B. K., Allred, E. N., Pirie-Shepherd, S. R., and Folkman, J. Continuous administration of endostatin by intraperitoneally implanted osmotic pump improves the efficacy and potency of therapy in a mouse xenograft tumor model. Cancer Research, 61: 7669-7674, 2001.
6. Tjin Tham Sjin, R. M., Satchi-Fainaro, R., Birsner, A. E., Ramanujam, V. M., Folkman, J., and Javaherian, K. A 27-amino-acid synthetic peptide corresponding to the NH2-terminal zinc-binding domain of endostatin is responsible for its antitumor activity. Cancer Research, 65: 3656-3663, 2005.

The invention claimed is:

1. A chimeric VEGF-binding protein comprising the amino acid sequence of SEQ ID NO: 3.

2. The chimeric VEGF-binding protein of claim 1, wherein the chimeric VEGF-binding protein consists of the amino acid sequence of SEQ ID NO: 3.

3. A pharmaceutical composition comprising the chimeric VEGF-binding protein of claim 1 and a pharmaceutically acceptable carrier.

4. The pharmaceutical composition of claim 3, wherein the pharmaceutical composition is a sustained-release pharmaceutical composition.

5. The pharmaceutical composition of claim 3, wherein the pharmaceutical composition is formulated for intratumoral administration.

6. The pharmaceutical composition of claim 3, wherein the pharmaceutical composition is formulated for intravenous administration.

7. The pharmaceutical composition of claim 3, wherein the pharmaceutical composition is formulated for topical administration.

8. A method of inhibiting angiogenesis in a subject in need thereof, the method comprising administering a therapeutically effective amount of the pharmaceutical composition of claim 3 to the subject.

9. The method of claim 8, wherein the subject has a cancer.

10. The method of claim 9, wherein the cancer is a cancer selected from the group consisting of: glioma, bladder cancer, breast cancer, colon cancer, melanoma, liver cancer, lung cancer, ovarian cancer, prostate cancer, renal cell carcinoma, hemangioma, and astrocytoma.

11. The method of claim 10, wherein the cancer is lung cancer.

12. The method of claim 8, wherein the subject has age-related macular degeneration.

13. The method of claim 8, wherein the subject has wet macular degeneration.

14. The method of claim 8, wherein the subject has diabetic retinopathy.

15. The method of claim 8, wherein the subject has an abnormal build-up or growth of blood vessels in the skin.

16. The method of claim 8, wherein the subject has a hemangioma.

17. The method of claim 8, wherein the subject has endometriosis.

18. A method of reducing blood vessel formation in a tumor in a subject, the method comprising administering a therapeutically effective amount of a pharmaceutical composition of claim 3 to the subject.

19. The method of claim 18, wherein the administering is performed using intratumoral or peritumoral administration.

20. The method of claim 18, wherein the tumor is a lung cancer tumor.

21. The method of claim 18, wherein the pharmaceutical composition is a sustained-release pharmaceutical composition.

* * * * *

SEQUENCE LISTING

```
<160> NUMBER OF SEQ ID NOS: 8

<210> SEQ ID NO 1
<211> LENGTH: 687
<212> TYPE: PRT
<213> ORGANISM: Homo sapiens

<400> SEQUENCE: 1

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160
```

```
Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575
```

```
Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
            595                 600                 605

Met Ala Ile Thr Lys Glu His Ser Ile Thr Leu Asn Leu Thr Ile Met
            610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Glu Ile Thr Ile Arg
            645                 650                 655

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
            675                 680                 685

<210> SEQ ID NO 2
<211> LENGTH: 469
<212> TYPE: PRT
<213> ORGANISM: Homo sapiens

<400> SEQUENCE: 2

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Val Val Gln
            20                  25                  30

Pro Gly Gly Ser Leu Arg Leu Ser Cys Ala Ala Ser Gly Phe Thr Phe
            35                  40                  45

Asp Asp Tyr Ala Met His Trp Val Arg Gln Ala Pro Gly Lys Gly Leu
50                  55                  60

Glu Trp Val Ser Leu Ile Ser Trp Asp Gly Gly Ser Thr Tyr Tyr Ala
65                  70                  75                  80

Asp Ser Val Lys Gly Arg Phe Thr Ile Ser Arg Asp Asn Ser Lys Asn
            85                  90                  95

Ser Leu Tyr Leu Gln Met Asn Ser Leu Arg Ala Glu Asp Thr Ala Leu
            100                 105                 110

Tyr Tyr Cys Ala Thr Arg Gly Gly Tyr Ser Thr Ala Gly Phe Asp Tyr
            115                 120                 125

Trp Gly Gln Gly Thr Leu Val Thr Val Ser Ser Ala Ser Thr Lys Gly
            130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270
```

```
Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 3
<211> LENGTH: 356
<212> TYPE: PRT
<213> ORGANISM: Artificial Sequence
<220> FEATURE:
<223> OTHER INFORMATION: VEGF-Trap 3

<400> SEQUENCE: 3

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160
```

-continued

Met Ile Ser Arg Thr Pro Glu Val Thr Cys Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 4
<211> LENGTH: 29
<212> TYPE: PRT
<213> ORGANISM: Artificial Sequence
<220> FEATURE:
<223> OTHER INFORMATION: Signal Peptide

<400> SEQUENCE: 4

Met Met Ser Phe Val Ser Leu Leu Leu Val Gly Ile Leu Phe Trp Ala
1               5                   10                  15

Thr Glu Ala Glu Gln Leu Thr Lys Cys Glu Val Phe Gln
            20                  25

<210> SEQ ID NO 5
<211> LENGTH: 27
<212> TYPE: PRT
<213> ORGANISM: Artificial Sequence
<220> FEATURE:
<223> OTHER INFORMATION: Signal Peptide

<400> SEQUENCE: 5

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser
            20                  25

<210> SEQ ID NO 6
<211> LENGTH: 1356
<212> TYPE: PRT
<213> ORGANISM: Homo sapiens

<400> SEQUENCE: 6

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
                100                 105                 110

Val Ile Tyr Val Tyr Val Gln Asp Tyr Arg Ser Pro Phe Ile Ala Ser
            115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
            195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
    275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Glu Ile Lys Trp Tyr Lys Asn Gly
    355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415
```

-continued

```
Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro His His Ile His Trp Tyr Trp Gln Leu Glu Glu
450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
        530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
        690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
        755                 760                 765

Val Gly Thr Ala Val Ile Ala Met Phe Phe Trp Leu Leu Leu Val Ile
770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
```

-continued

```
            835                 840                 845
Ile Glu Ala Asp Ala Phe Gly Ile Asp Lys Thr Ala Thr Cys Arg Thr
        850                 855                 860
Val Ala Val Lys Met Leu Lys Glu Gly Ala Thr His Ser Glu His Arg
865                 870                 875                 880
Ala Leu Met Ser Glu Leu Lys Ile Leu Ile His Ile Gly His His Leu
                885                 890                 895
Asn Val Val Asn Leu Leu Gly Ala Cys Thr Lys Pro Gly Gly Pro Leu
        900                 905                 910
Met Val Ile Val Glu Phe Cys Lys Phe Gly Asn Leu Ser Thr Tyr Leu
                915                 920                 925
Arg Ser Lys Arg Asn Glu Phe Val Pro Tyr Lys Thr Lys Gly Ala Arg
        930                 935                 940
Phe Arg Gln Gly Lys Asp Tyr Val Gly Ala Ile Pro Val Asp Leu Lys
945                 950                 955                 960
Arg Arg Leu Asp Ser Ile Thr Ser Ser Gln Ser Ser Ala Ser Ser Gly
                965                 970                 975
Phe Val Glu Glu Lys Ser Leu Ser Asp Val Glu Glu Glu Glu Ala Pro
        980                 985                 990
Glu Asp Leu Tyr Lys Asp Phe Leu Thr Leu Glu His Leu Ile Cys Tyr
                995                1000                1005
Ser Phe Gln Val Ala Lys Gly Met Glu Phe Leu Ala Ser Arg Lys
        1010                1015                1020
Cys Ile His Arg Asp Leu Ala Ala Arg Asn Ile Leu Leu Ser Glu
        1025                1030                1035
Lys Asn Val Val Lys Ile Cys Asp Phe Gly Leu Ala Arg Asp Ile
        1040                1045                1050
Tyr Lys Asp Pro Asp Tyr Val Arg Lys Gly Asp Ala Arg Leu Pro
        1055                1060                1065
Leu Lys Trp Met Ala Pro Glu Thr Ile Phe Asp Arg Val Tyr Thr
        1070                1075                1080
Ile Gln Ser Asp Val Trp Ser Phe Gly Val Leu Leu Trp Glu Ile
        1085                1090                1095
Phe Ser Leu Gly Ala Ser Pro Tyr Pro Gly Val Lys Ile Asp Glu
        1100                1105                1110
Glu Phe Cys Arg Arg Leu Lys Glu Gly Thr Arg Met Arg Ala Pro
        1115                1120                1125
Asp Tyr Thr Thr Pro Glu Met Tyr Gln Thr Met Leu Asp Cys Trp
        1130                1135                1140
His Gly Glu Pro Ser Gln Arg Pro Thr Phe Ser Glu Leu Val Glu
        1145                1150                1155
His Leu Gly Asn Leu Leu Gln Ala Asn Ala Gln Gln Asp Gly Lys
        1160                1165                1170
Asp Tyr Ile Val Leu Pro Ile Ser Glu Thr Leu Ser Met Glu Glu
        1175                1180                1185
Asp Ser Gly Leu Ser Leu Pro Thr Ser Pro Val Ser Cys Met Glu
        1190                1195                1200
Glu Glu Glu Val Cys Asp Pro Lys Phe His Tyr Asp Asn Thr Ala
        1205                1210                1215
Gly Ile Ser Gln Tyr Leu Gln Asn Ser Lys Arg Lys Ser Arg Pro
        1220                1225                1230
Val Ser Val Lys Thr Phe Glu Asp Ile Pro Leu Glu Glu Pro Glu
        1235                1240                1245
```

```
Val Lys  Val Ile Pro Asp Asp  Asn Gln Thr Asp Ser  Gly Met Val
    1250                 1255                 1260

Leu Ala  Ser Glu Glu Leu Lys  Thr Leu Glu Asp Arg  Thr Lys Leu
    1265                 1270                 1275

Ser Pro  Ser Phe Gly Gly Met  Val Pro Ser Lys Ser  Arg Glu Ser
    1280                 1285                 1290

Val Ala  Ser Glu Gly Ser Asn  Gln Thr Ser Gly Tyr  Gln Ser Gly
    1295                 1300                 1305

Tyr His  Ser Asp Asp Thr Asp  Thr Thr Val Tyr Ser  Ser Glu Glu
    1310                 1315                 1320

Ala Glu  Leu Leu Lys Leu Ile  Glu Ile Gly Val Gln  Thr Gly Ser
    1325                 1330                 1335

Thr Ala  Gln Ile Leu Gln Pro  Asp Ser Gly Thr Thr  Leu Ser Ser
    1340                 1345                 1350

Pro Pro  Val
    1355

<210> SEQ ID NO 7
<211> LENGTH: 26
<212> TYPE: PRT
<213> ORGANISM: Artificial Sequence
<220> FEATURE:
<223> OTHER INFORMATION: Signal Peptide

<400> SEQUENCE: 7

Met Gln Ser Lys Val Leu Leu Ala Val Ala Leu Trp Leu Cys Val Glu
1               5                   10                  15

Thr Arg Ala Ala Ser Val Gly Leu Pro Ser
            20                  25

<210> SEQ ID NO 8
<211> LENGTH: 1071
<212> TYPE: DNA
<213> ORGANISM: Artificial Sequence
<220> FEATURE:
<223> OTHER INFORMATION: Chimeric VEGF-binding protein

<400> SEQUENCE: 8
atggtgagct actgggacac tggggtgctg ctgtgtgccc tgctgagctg cctgctgctg     60
actggcagca gctctggctc tgacactggc aggccctttg tggagatgta ctctgagatc    120
cctgagatca tccacatgac tgagggcagg gagctggtga tcccctgcag agtgaccagc    180
cccaacatca ctgtgaccct gaagaagttc cccctggaca ccctgatccc tgatggcaag    240
aggatcatct gggacagcag gaagggcttc atcatcagca atgccaccta caaggagatt    300
ggcctgctga cctgtgaggc cactgtgaat ggccacctgt acaagaccaa ctacctgacc    360
cacaggcaga ccaacaccat catcgatgac aaaactcaca catgcccacc gtgcccagca    420
cctgaactcc tggggggacc gtcagtcttc ctcttccccc caaaacccaa ggacaccctc    480
atgatctccc ggacccctga ggtcacatgc gtggtggtgg acgtgagcca cgaagaccct    540
gaggtcaagt tcaactggta cgtggacggc gtggaggtgc ataatgccaa gacaaagccg    600
cgggaggagc agtacaacag cacgtaccgt gtggtcagcg tcctcaccgt cctgcaccag    660
gactggctga atggcaagga gtacaagtgc aaggtctcca acaaagccct cccagccccc    720
atcgagaaaa ccatctccaa agccaaaggg cagccccgag agccacaggt gtacaccctg    780
cccccatccc gggatgagct gaccaagaac caggtcagcc tgacctgcct ggtcaaaggc    840
```

```
ttctatccca gcgacatcgc cgtggagtgg gagagcaatg ggcagccgga gaacaactac    900
aagaccacgc ctcccgtgct ggactccgac ggctccttct tcctctacag caagctcacc    960
gtggacaaga gcaggtggca gcaggggaac gtcttctcat gctccgtgat gcatgaggct   1020
ctgcacaacc actacacgca gaagagcctc tccctgtctc cgggtaaatg a            1071
```